(12) United States Patent
Kim et al.

(10) Patent No.: US 8,030,274 B2
(45) Date of Patent: Oct. 4, 2011

(54) METHOD FOR TREATING ASTHMA AND CHRONIC OBSTRUCTIVE PULMONARY DISEASE (COPD) COMPRISING ADMINISTERING FGF2

(75) Inventors: Yoon-Keum Kim, Seoul (KR); Soo Hyung Kang, Yongin-si (KR); Byong Moon Kim, Seoul (KR); Miwon Son, Sungnam-si (KR)

(73) Assignee: Dong-A Pharmaceutical Co., Ltd., Seoul (KR)

( * ) Notice: Subject to any disclaimer, the term of this patent is extended or adjusted under 35 U.S.C. 154(b) by 434 days.

(21) Appl. No.: 11/568,896

(22) PCT Filed: May 12, 2005

(86) PCT No.: PCT/KR2005/001390
§ 371 (c)(1),
(2), (4) Date: Nov. 9, 2006

(87) PCT Pub. No.: WO2005/107794
PCT Pub. Date: Nov. 17, 2005

(65) Prior Publication Data
US 2008/0172751 A1    Jul. 17, 2008

(30) Foreign Application Priority Data
May 12, 2004 (KR) .......... 10-2004-0033261

(51) Int. Cl.
*A61K 38/18* (2006.01)
*C07K 14/50* (2006.01)
(52) U.S. Cl. ........................... 514/9.1; 530/399
(58) Field of Classification Search .......... None
See application file for complete search history.

(56) References Cited

U.S. PATENT DOCUMENTS
5,514,652 A    5/1996  Watanuki et al.
2003/0040496 A1   2/2003  Chandler et al.

FOREIGN PATENT DOCUMENTS
CN    1524577    9/2004

OTHER PUBLICATIONS

Kranenburg et al. J. Pathol. 206: 28-38, 2005.*
Kranenburg et al. (Am. J. Respir. Cell Mol. Biol. 27: 517-525, 2002).*
Evans, et al., Fibroblast Growth Factor-2 in Remodeling of the Developing Basement Membrane Zone in the Trachea of Infant Rhesus Monkeys Sensitized and Challenged with Allergen, Laboratory Investigation 82:1747-1754, 2002.
Redington, et al., Basic Fibroblast Growth Factor in Asthma: Measurement in Bronchoalveolar Lavage Fluid Basally and Following Allergen Challenge, Journal of Allergy and Clinical Immunology, 107(2): 384-387, 2001.
Hoshino, et al., Expression of Vascular Endothelial Growth Factor, Basic Fibroblast Growth Factor, and Angiogenin Immunoreactivity in Asthmatic Airways and its Relationship to Angiogenesis, Journal of Allergy and Clinical Immunology, 107(2):295-301, 2001.

* cited by examiner

*Primary Examiner* — Christine J Saoud
(74) *Attorney, Agent, or Firm* — Lucas & Mercanti, LLP

(57) ABSTRACT

The present invention relates an agent comprising FGF2 (Fibroblast Growth Factor-2 or basic Fibroblast Growth Factor (bFGF)) as an effective ingredient for treatment or prevention of Asthma and Chronic Obstructive Pulmonary Disease (COPD). Also, The present invention relates Th1 asthma and COPD mouse animal model induced by Ovalbumin and double strand RNA. The therapeutic agent comprising FGF2 of the present invention can be used for treatment or prevention for airway fibrosis, airway inflammation, airway hyperresponsiveness, airway remodeling, asthma and COPD. Also, Th1 asthma and COPD mice animal model induced by Ovalbumin and double strand RNA can be used for development of therapeutic agent for asthma and COPD.

1 Claim, 16 Drawing Sheets

[Fig. 1]
A
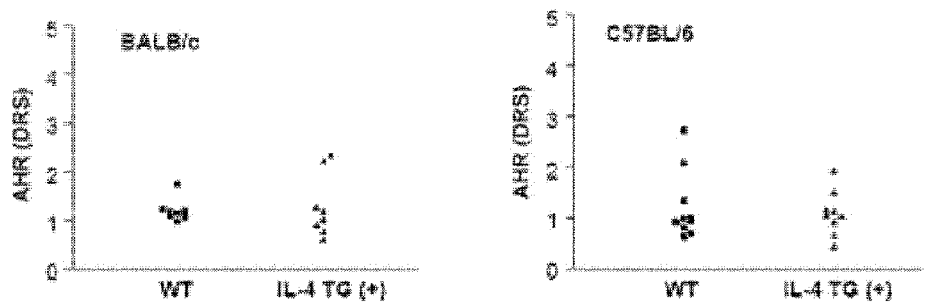
B
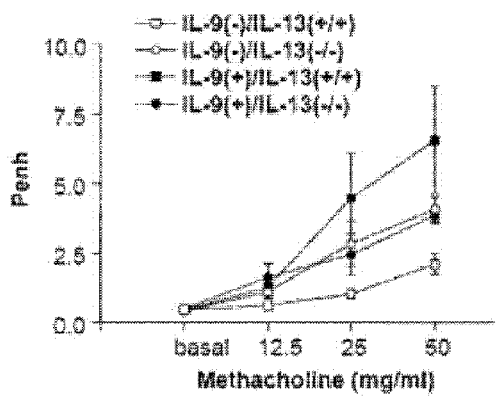
[Fig. 2]
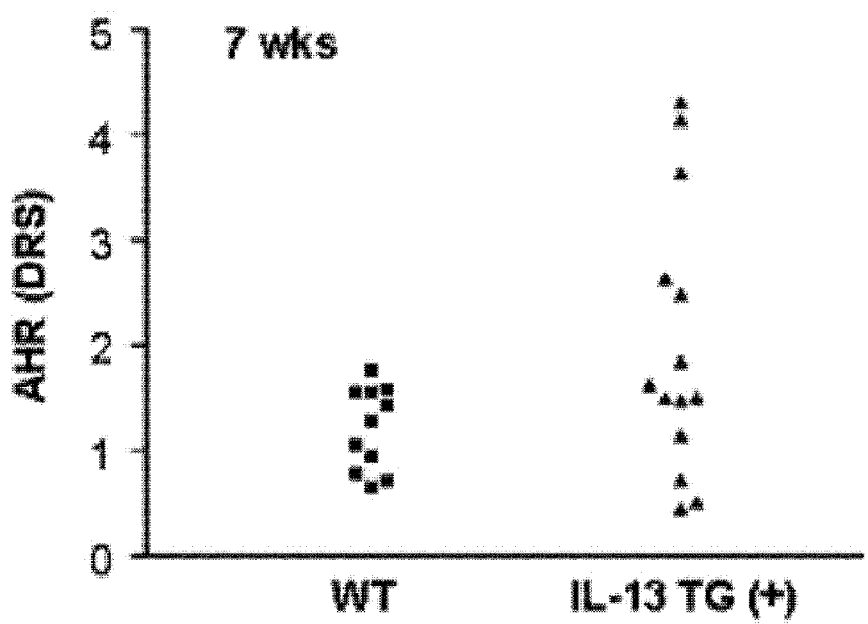

[Fig. 3]
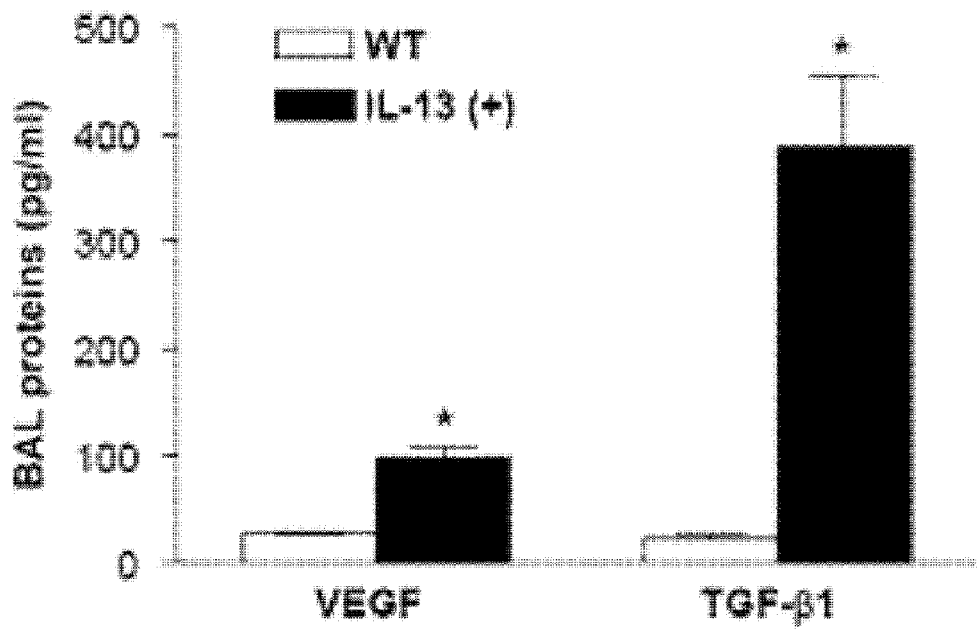
[Fig. 4]
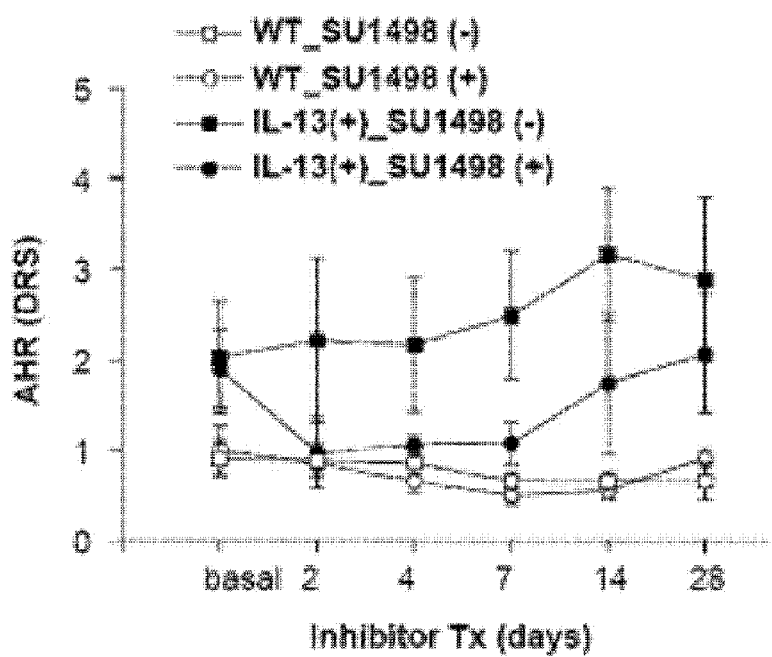

[Fig. 5]
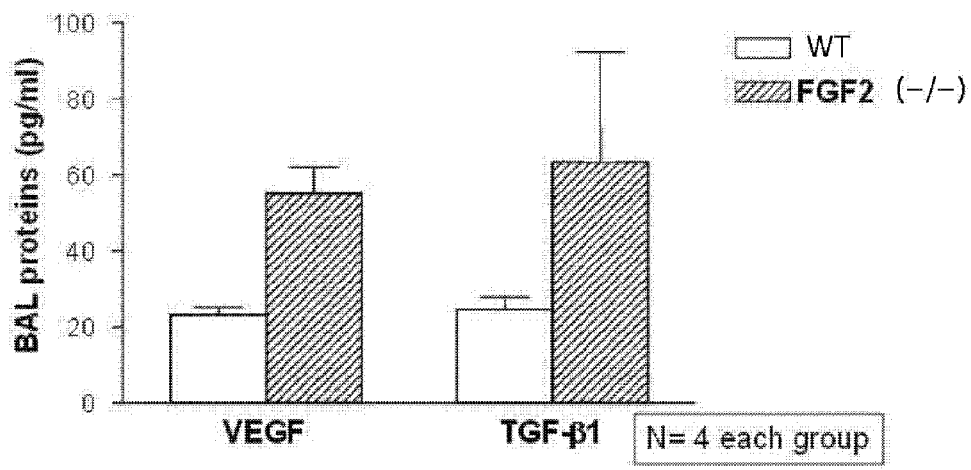
[Fig. 6]
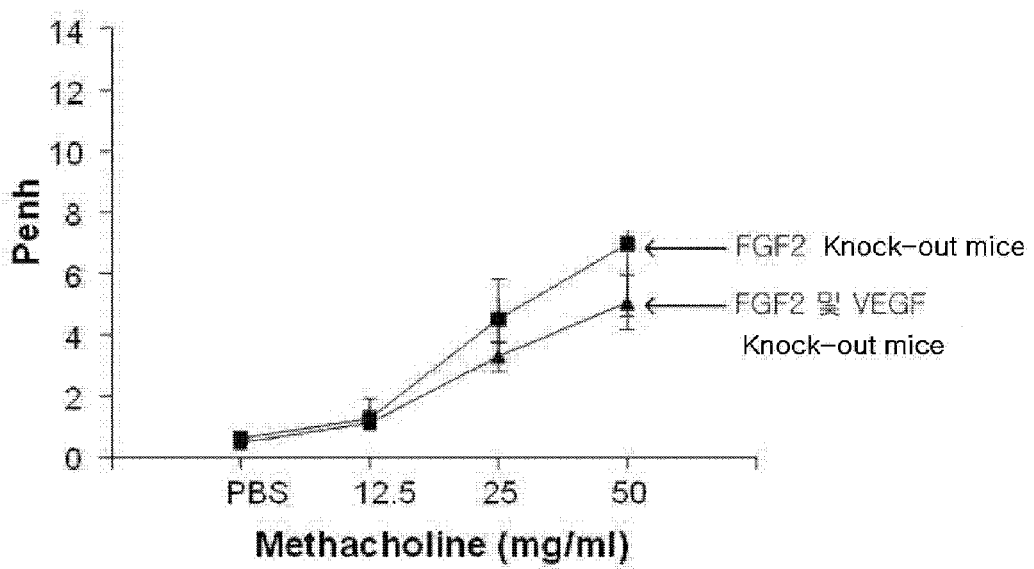

[Fig. 7]
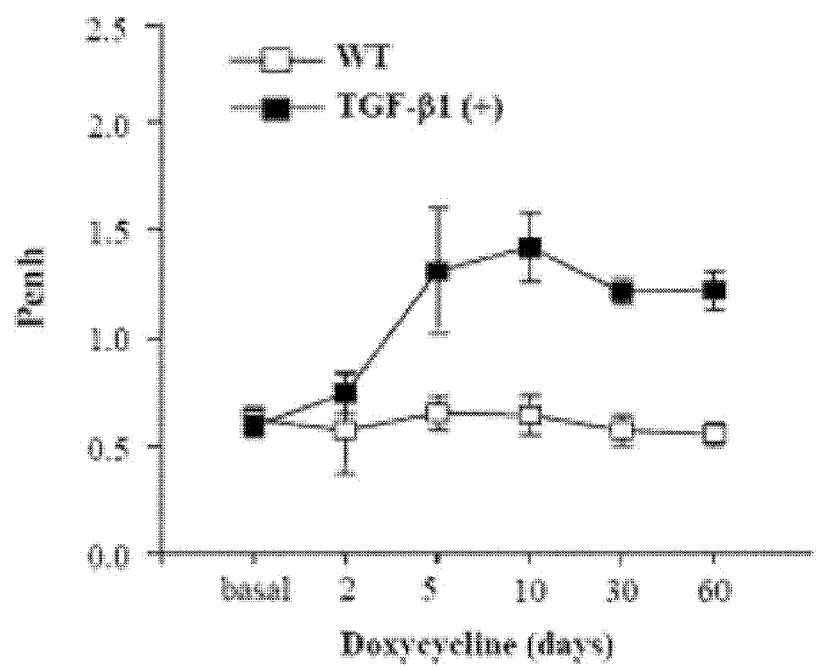
[Fig. 8]
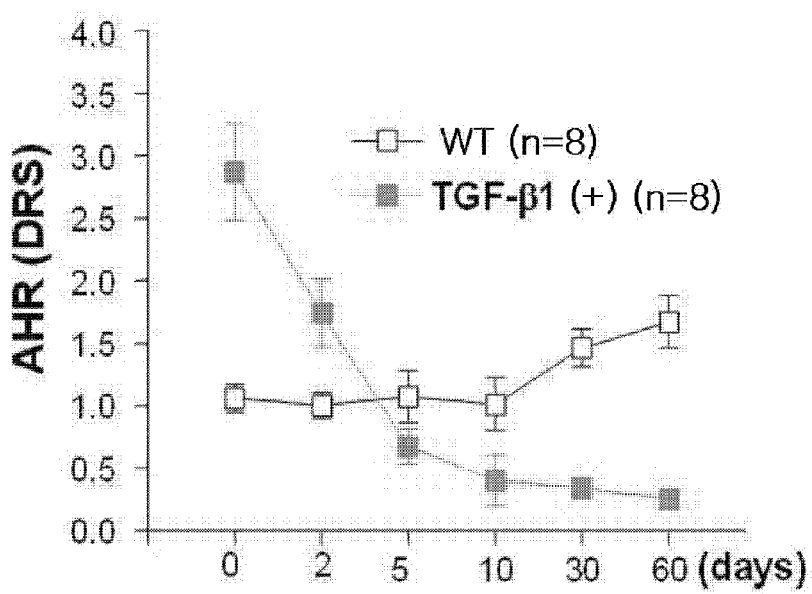

[Fig. 9]
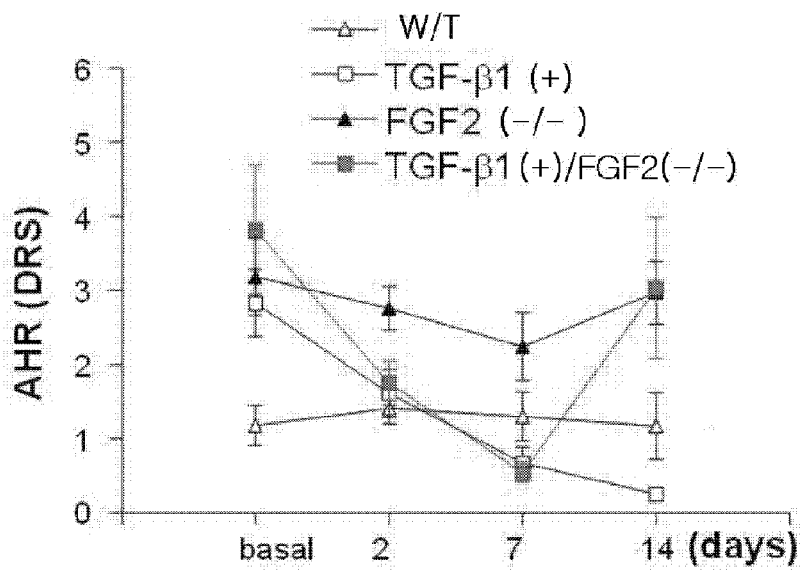
[Fig. 10]
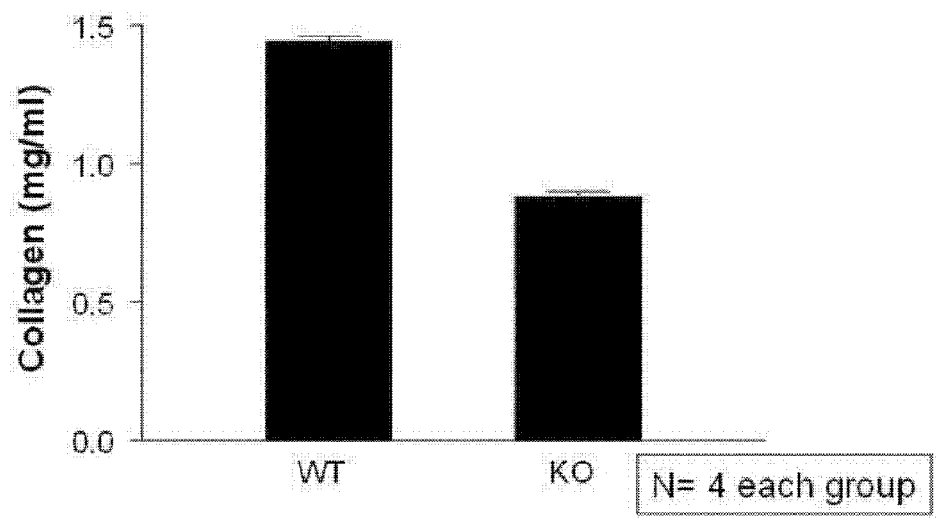

[Fig. 11]
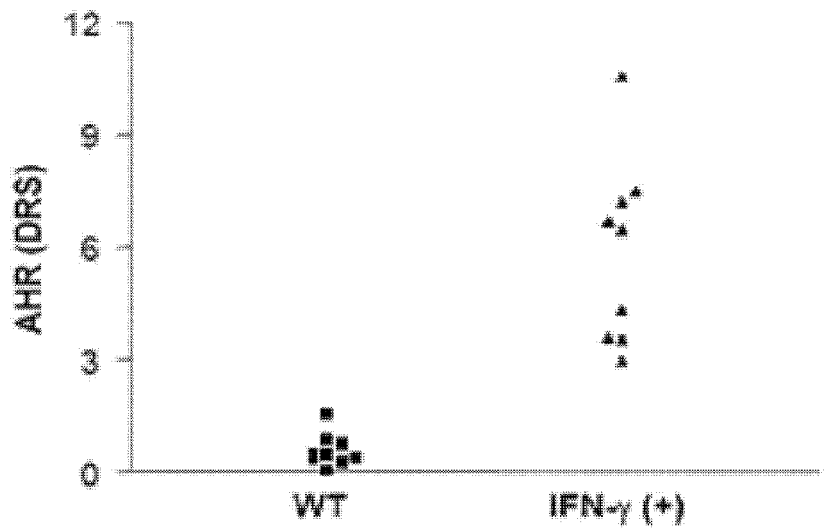
[Fig. 12]
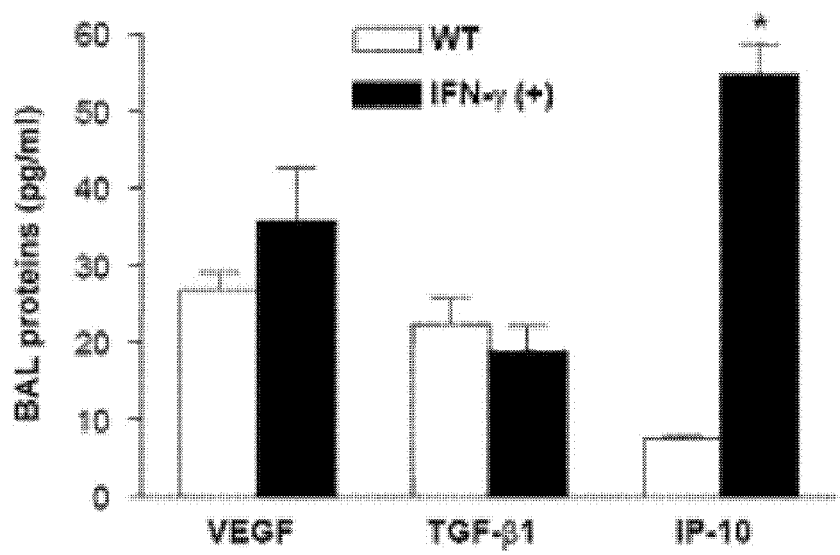

[Fig. 13]
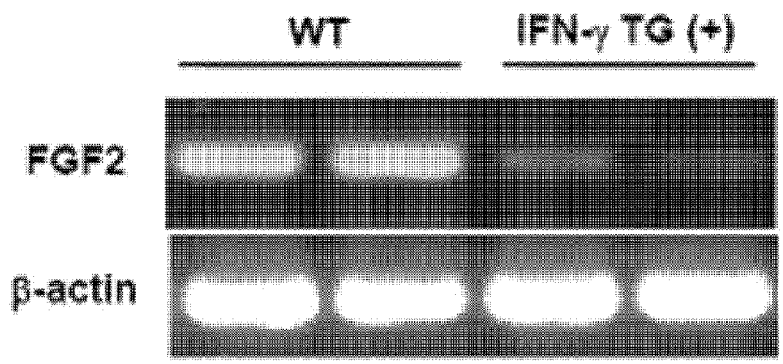
[Fig. 14]
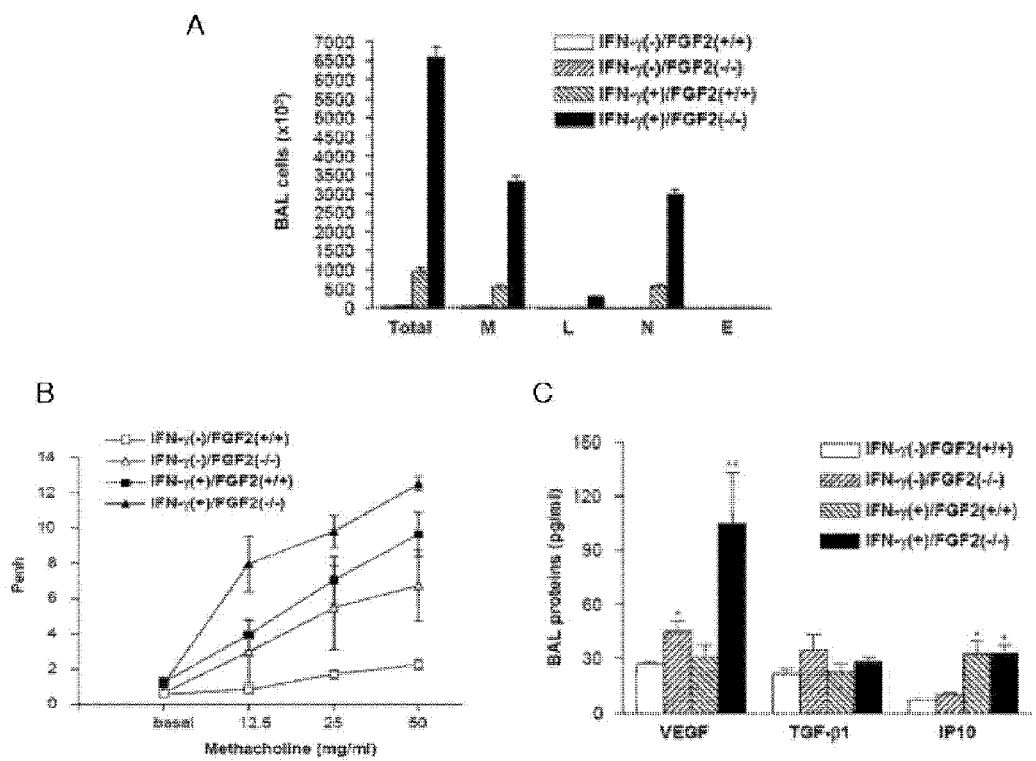

[Fig. 15]
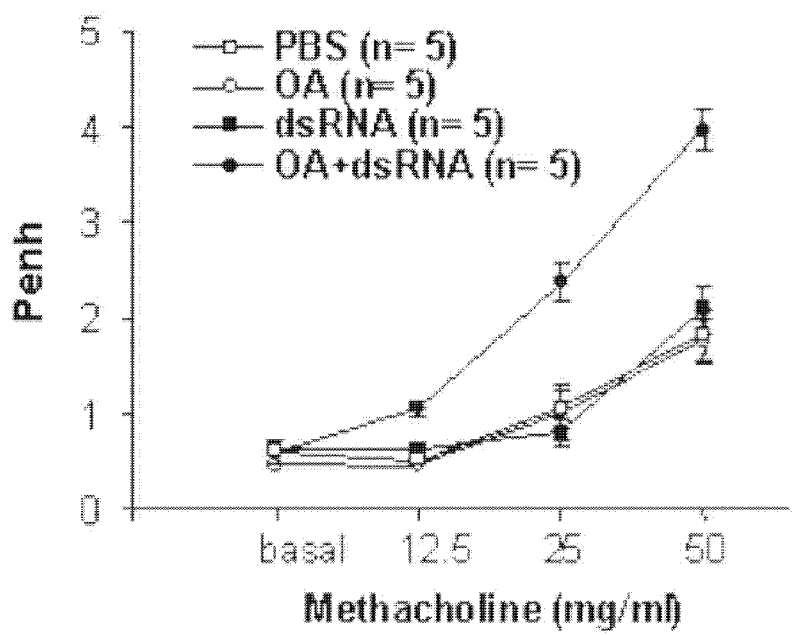
[Fig. 16]
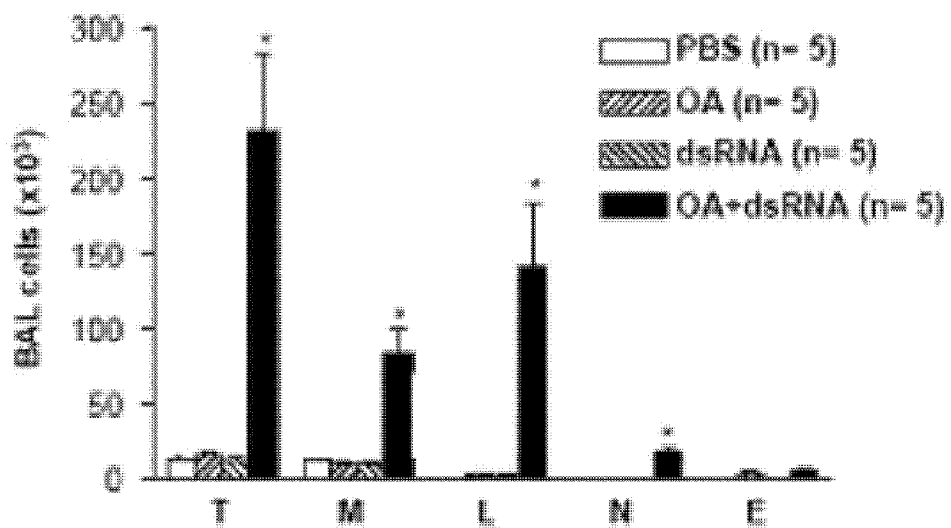

[Fig. 17]
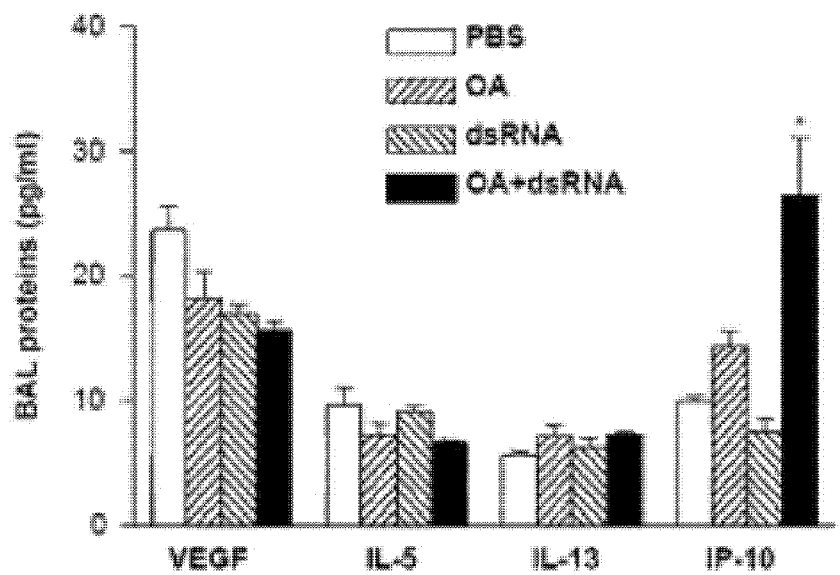
[Fig. 18]
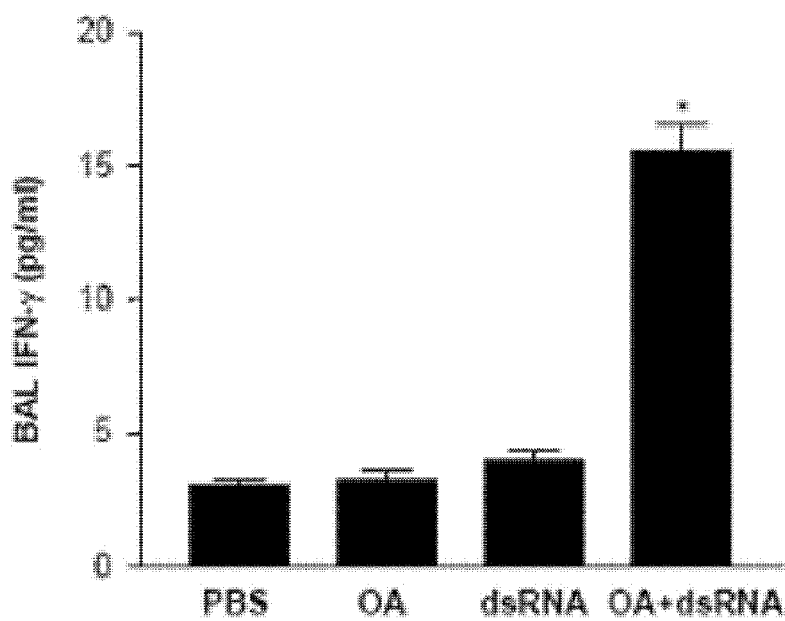

[Fig. 19]
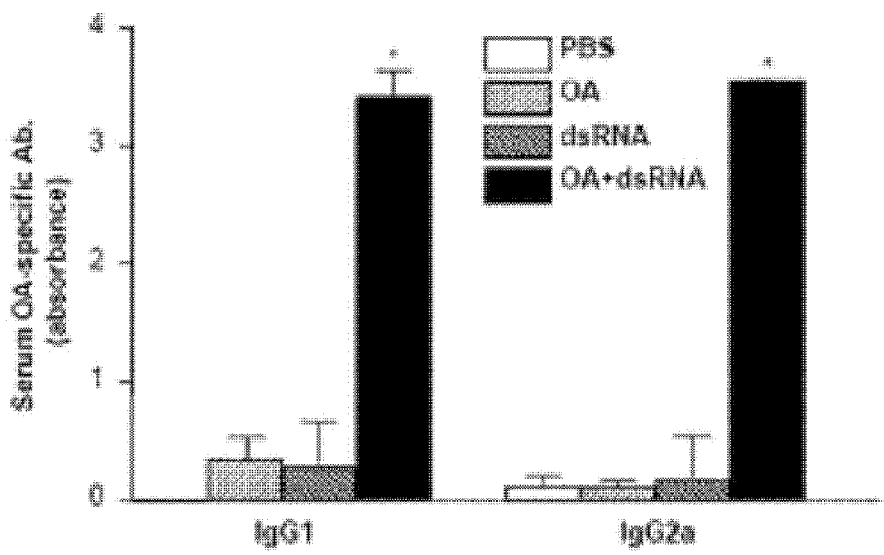
[Fig. 20]
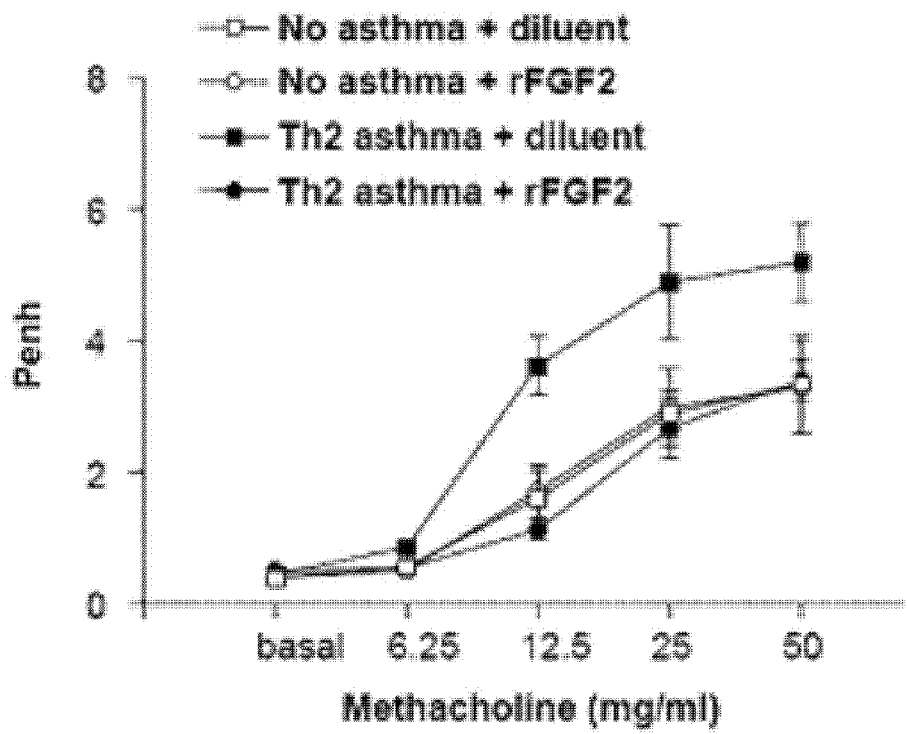

[Fig. 21]
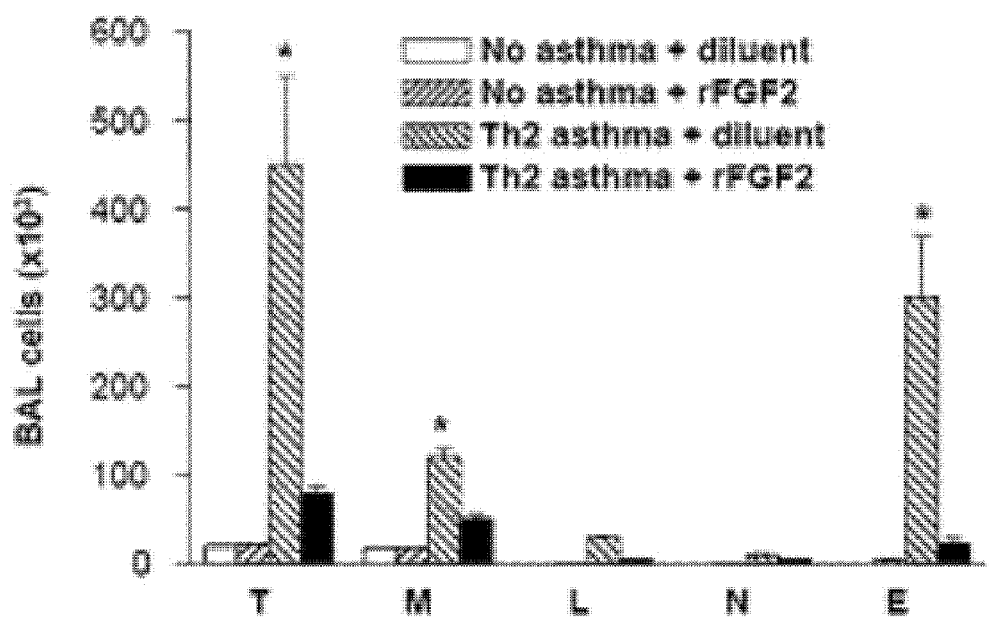
[Fig. 22]
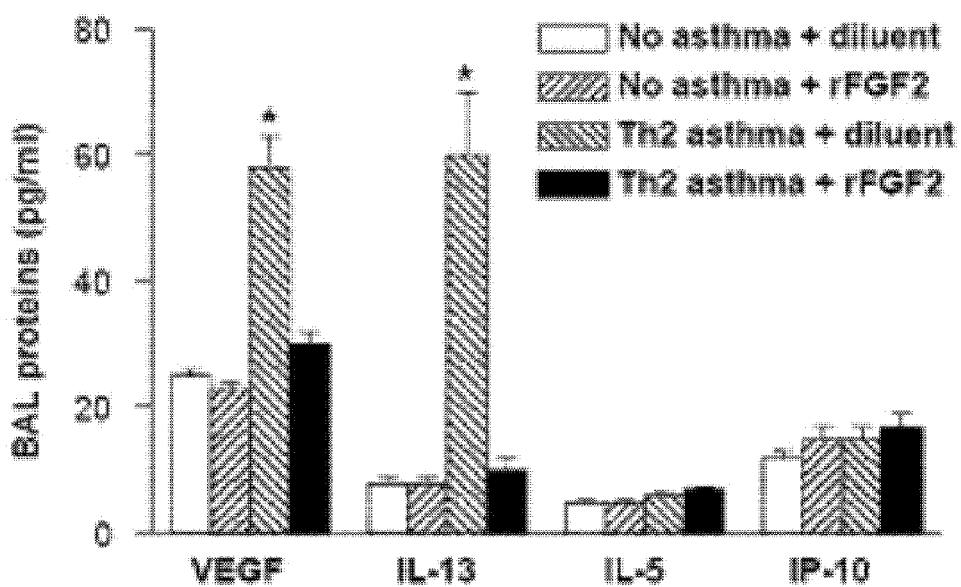

[Fig. 23]
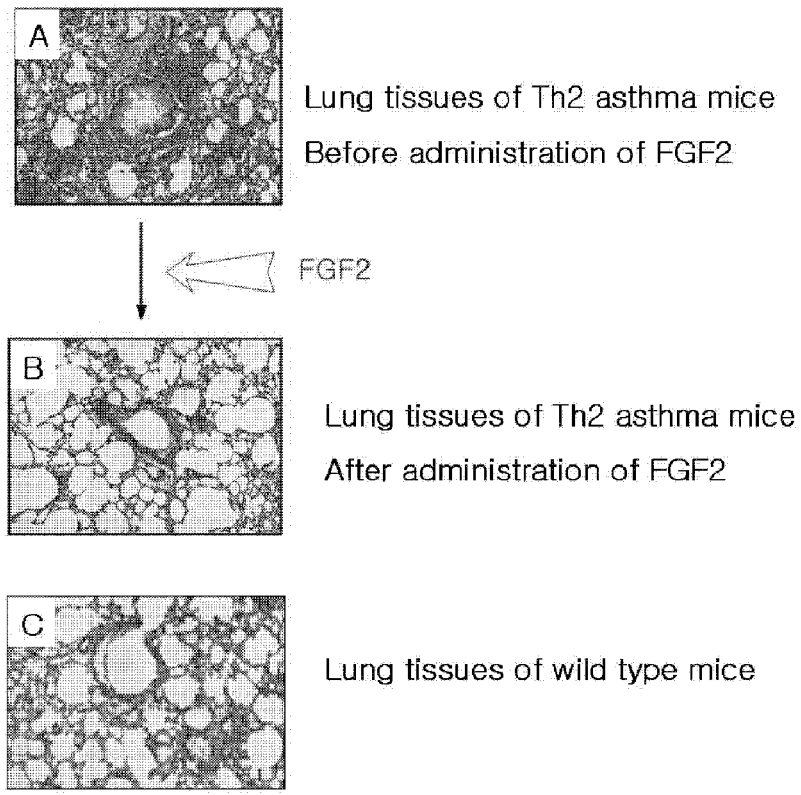
Lung tissues of Th2 asthma mice
Before administration of FGF2
Lung tissues of Th2 asthma mice
After administration of FGF2
Lung tissues of wild type mice
[Fig. 24]
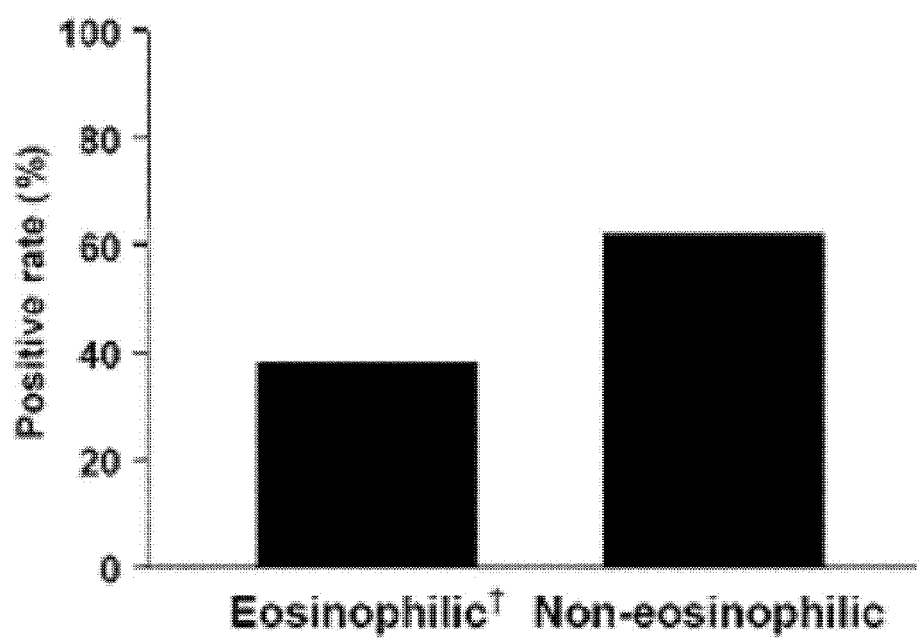

[Fig. 25]
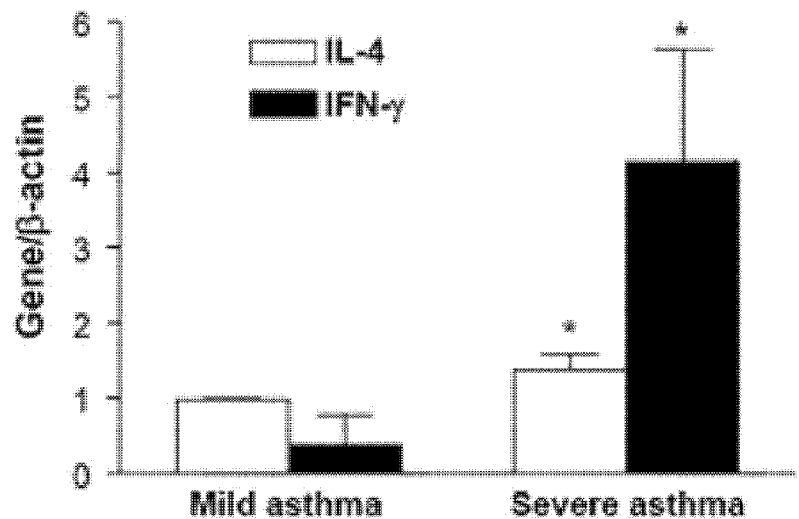
[Fig. 26]
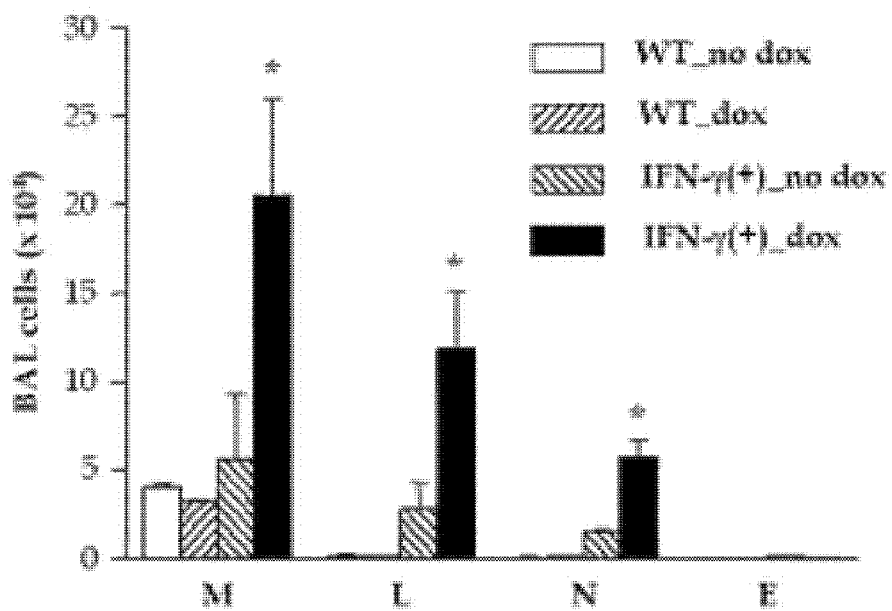

[Fig. 27]
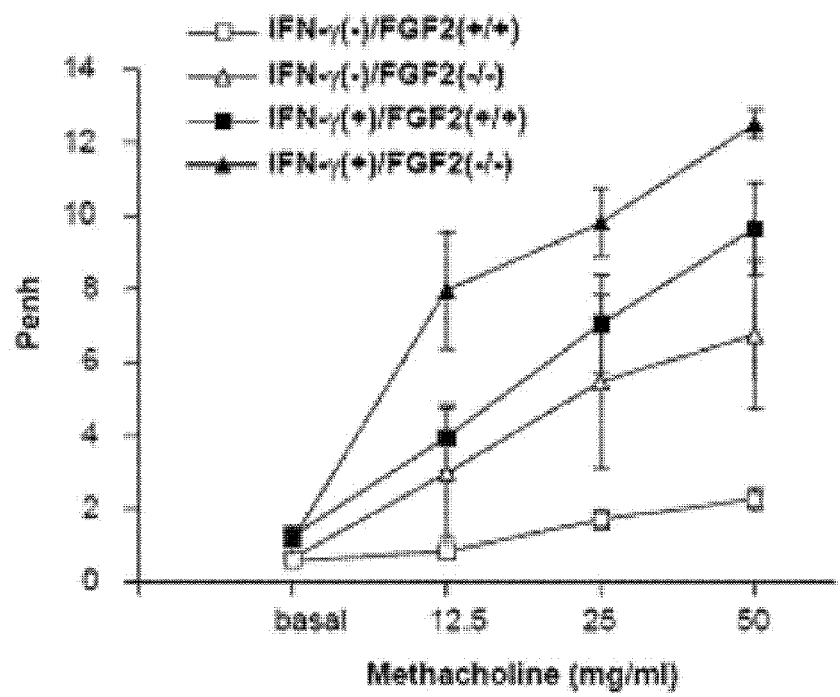
[Fig. 28]
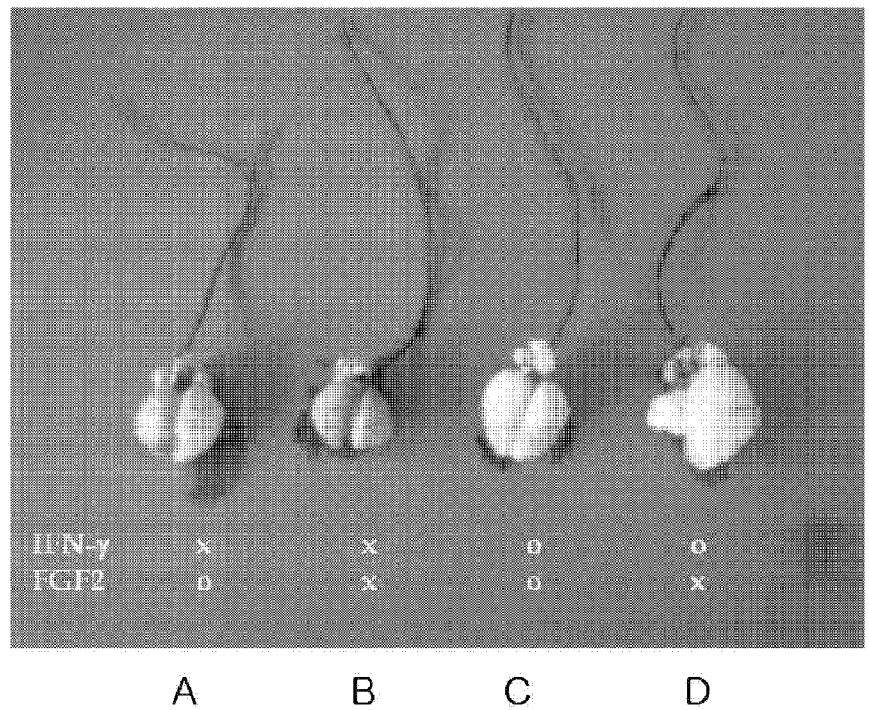

[Fig. 29]
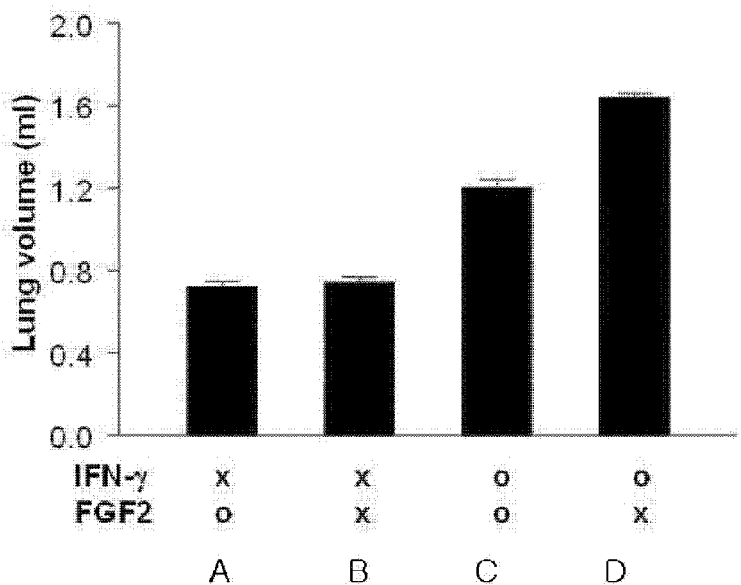
[Fig. 30]
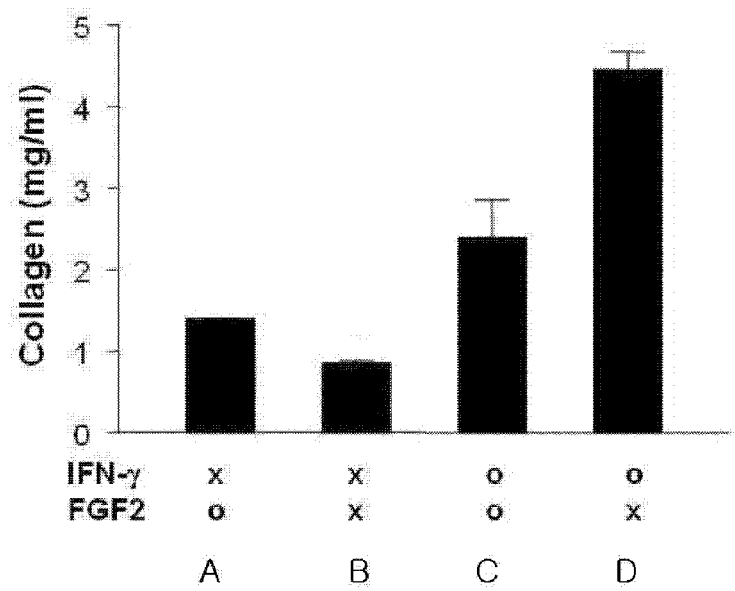

[Fig. 31]
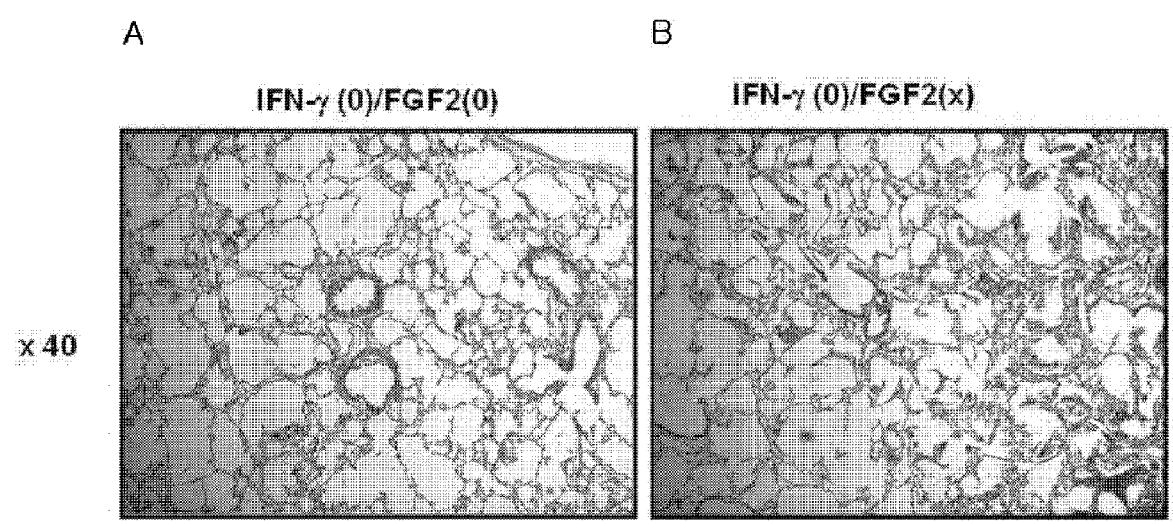

SEQUENCE LISTING

<160> NUMBER OF SEQ ID NOS: 2

<210> SEQ ID NO 1
<211> LENGTH: 22
<212> TYPE: DNA
<213> ORGANISM: Artificial Sequence
<220> FEATURE:
<223> OTHER INFORMATION: Primer

<400> SEQUENCE: 1
actcacattc gaaacccaa ac                     22

<210> SEQ ID NO 2
<211> LENGTH: 19
<212> TYPE: DNA
<213> ORGANISM: Artificial Sequence -continued

```
<220> FEATURE:
<223> OTHER INFORMATION: Primer

<400> SEQUENCE: 2
cgtcagatcg cctggagac                                              19
```

METHOD FOR TREATING ASTHMA AND CHRONIC OBSTRUCTIVE PULMONARY DISEASE (COPD) COMPRISING ADMINISTERING FGF2

CROSS-REFERENCE TO RELATED APPLICATIONS

This application is a 371 of PCT/KR2005/001390 filed on May 12, 2005, which claims the benefit of Korean Patent Application No. 10-2004-0033261 filed on May 12, 2004, the contents of each of which are incorporated herein by reference.

TECHNICAL FIELD

The present invention relates to an agent containing FGF2 (Fibroblast Growth Factor-2, or basic Fibroblast Growth Factor, bFGF) as an effective ingredient for the prevention and the treatment of asthma and chronic obstructive pulmonary disease (COPD). The present invention also relates to a mouse model of COPD and Th1 asthma induced by ovalbumin (OA) and double stranded RNA (dsRNA).

BACKGROUND ART

In the past 20 years, the prevalence of asthma has almost doubled, and today asthma affects 8-10% of the world's population. Asthma is a chronic inflammatory disorder of the airways and is characterized by airway hyperresponsiveness (AHR) to nonspecific stimuli and airway remodeling, which is associated with alterations in the structures and functions of the elements involved like fibroblast and myofibroblasts. Asthma is largely divided into bronchial asthma and cardiac asthma, but in general asthma means simply bronchial asthma.

One of the most representative pulmonary diseases, along with asthma, is chronic obstructive pulmonary disease (COPD) which is distinguished from asthma by accompanying obstruction of airway. COPD takes the 4 place in the causes of death world-widely and the development rate of only COPD among 10 most significant diseases is increasing. COPD is caused by pathological alterations in bronchioles and parenchyma resulted from continuous inflammation in airway and parenchyma, and so is characterized by obliterative bronchiolitis and pulmonary emphysema (the destruction of parenchyma). Chronic obstructive pulmonary diseases are exemplified by chronic obstructive bronchitis, chronic bronchiolitis and emphysema.

The treatment of asthma and such chronic obstructive pulmonary diseases has depended on using anti-inflammatory agents or bronchodilators. Glucocorticoids, leukotriene modifiers and theophyllines are the representative anti-inflammatory agents.

Although the glucocorticoid has a strong medicinal efficacy, it does not work for a specific target but for the inhibition of all immune and anti-inflammatory responses, meaning it inhibits necessary immune responses, too, and it carries serious side effects, requiring inhalation therapy. Luekotriene modifiers have fewer side effects but are limited in medicinal effects, so that they cannot regulate asthma independently and can only be used as a subsidiary. Theophylline also has problems of weak medicinal effect and side effects.

Therefore, it is required to develop an asthma treating agent with strong effect but fewer side effects. And for the development of such agents, full understanding on the developmental mechanism of asthma is prerequisite.

It is a generally accepted theory that type 1 helper T cells (Th1) or type 2 helper T cells (Th2) secret cytokines which play an important role in the development of asthma, more precisely, unbalance between cytokines, from Th1 and Th2, causes asthma (Th1/Th2 hypothesis) (Mosmann et al., J. Immunol., 136: 2348-57, 1986; Robinson et al., N. Engl. J. Med., 326: 298-304, 1992; Grunig et al., Science, 282: 2261-3, 1998; Richter et al., Am. J. Respir. Cell Mol. Biol., 25: 385-91, 2001). However, an exact mechanism of asthma induced by cytokines has not been explained, yet.

Interleukin-13 (IL-13), produced by activated Th2 lymphocytes, is a key cytokine in the pathogenesis of asthma (Grunig et al., Science, 282: 2261-3, 1998). It is supported by the findings that airway hyperresponsiveness was inhibited by suppressing the expression of IL-13 in an allergic asthma animal model but was induced again when recombinant IL-13 was administered through airway (Marsha et al., Science, 282: 2258-2261, 1998). Histological report shown in IL-13 transgenic mice was similar to that observed in asthma patients, and over-expression of IL-13 induced inflammation in airway, increase of mucus secretion and fibrosis of epithelial cells (Zhu et al., J. Clin. Invest., 103:779-788, 1999).

The idea that IL-13 can enhance AHR by promoting the infiltration of inflammatory cells, especially eosinophils, remains popular (Hargreave et al., J. Allergy clin. Immunol., 78: 825-32, 1986). However, recent evidence suggests that the induction of AHR can occur in the absence of eosinophil infiltration (Venkayya et al., Am. J. Respir. Cell Mol. Biol. 26: 202-8, 2002).

Transforming Growth Factor β1 (TGF-β1) or Vascular Endothelial Growth Factor (VEGF) is known to be involved in pathogenesis of asthma induced by IL-13 (Lee et al., Nat. Med., 10: 1095-1103, 2004).

TGF-β1, as a key element to heal the wound of tissues, induces tissue fibrosis which is a major pathological change in airway remodeling. Precisely, TGF-β1 changes fibroblasts into myofibroblasts, then myofibroblasts secret collagen more than resting fibroblasts, resulting in airway remodeling by tissue fibrosis (Vignola et al., Am. J. Respir. Crit. Care Med., 156: 591-599, 1997). This is in accordance with the finding of previous study that fibrosis in lung was induced mainly by TGF-β1 dependent pathway in IL-13 transgenic mice (Lee et al., J. Exp. Med., 194: 809-21, 2001).

During the process of tissue fibrosis, TGF-β1 induces the secretions of fibroblast growth factor-2 (FGF2 or basic Fibroblast Growth Factor, bFGF) and its receptor-1 (FGFR-1) or FGF receptor-2 (FGFR-2). FGF2 is known to be associated with the proliferation of endothelial cells or smooth muscle cells and also play an important role in angiogenesis (Nugent et al., Int. J. Biochem. Cell Biol. 32: 115-20, 2000). However, the role of FGF2 in pathogenesis of asthma and AHR has been still in question.

Vascular endothelial growth factor (VEGF) is a kind of cytokine that increases penetration of plasma protein through blood capillaries, promotes differentiation and migration of cells and induces the secretion of protease reforming a cell. VEGF is also involved in the maintenance of new blood vessels by inhibiting apoptosis, in the regulation of immune response by suppressing neuronal antigen and in the induction of cell growth and division. The present inventors demonstrated that there is a positive feedback loop between IL-13 and VEGF in relation to immune response against antigens and foreign materials (Lee et al., Nat. Med., 10: 1095-1103, 2004). Though, a role of FGF2 in pathogenesis of VEGF mediated asthma has not been elucidated.

Interferon-γ(IFN-γ) is another key cytokine secreted by Th1, in relation to the pathogenesis of asthma. Precisely, IFN-γ is a substance secreted in Th1 lymphocytes as a defender against pathogen (Fong et al., J. Imunol., 143: 2887-93, 1989), and is known to inhibit the production of Th2 cytokine (Mosann et al., J. Immunol., 136: 2348-57, 1986). Based on the Th1/Th2 hypothesis, IFN-γ has been believed to inhibit asthma, which still remains controversial. According to previous studies contradictory to the belief, airway remodeling similar to that of asthma patients is observed in IFN-γ transgenic mice (Wang et al., J. Exp. Med., 192: 1587-1600, 2000) and in particular, the severity of asthma is significantly related to the increase of IFN-γ (Corrogan et al., Lancet 1: 1129-32, 1988; Mognan et al., Am. J. Respir. Crit. Care Med., 161: 1790-6, 2000).

This contradictory idea is also supported by the founding that asthma treating agents widely used such as corticosteroids, β2-adrenergic agonists and methylxanthine derivatives, inhibit rather Th1 immune response than Th2 immune response. Thus, it is limited in explaining pathogenesis of asthma with Th1/Th2 hypothesis emphasizing the importance of promoting Th2 immune response.

In the meantime, the involvement of COPD in pathogenesis of asthma has not been elucidated, either. That is, the development and the progress of COPD has not been explained, so it is required to give full explanation on the exact mechanism of the above prior to the development of a therapeutic agent for COPD.

According to the results of recent studies with transgenic mice, IFN-γ (Wang et al., J. Exp. Med., 192: 1587-600, 2000) and IL-13 (Zheng et al., J. Clin. Invest., 106: 1081-93, 2000) proved to be involved in pathogenesis of asthma, are elements inducing pathological phenomena similar to those of human COPD. As mentioned hereinbefore, cytokines are largely secreted in immune cells, suggesting that immune response plays a key role in pathogenesis of COPD. IFN-γ and IL-13 are important factors alleviating inflammation in airway and parenchyma. For the healing of wound initiated by inflammation, the balance between attackers and defenders during the restoration of airway and pulmonary epithelial cells is particularly important (Lee et al., J. Exp. Med., 200: 377-89, 2004), which is high occupation of attackers or short of defenders might cause COPD.

The present inventors investigated the role of FGF2 in pathogenesis of IL-13, TGF-β1, VEGF and IFN-γ mediated asthma and COPD and confirmed that FGF2 suppresses AHR, induced by VEGF stimulated by IL-13 or induced by IFN-γ and inhibits pulmonary emphysema initiated by inflammation in airway and parenchyma, so that FGF2 can be effectively used for the prevention and the treatment of asthma and COPD.

And, the present inventors completed this invention by creating Th1 asthma and COPD animal models induced by ovalbumin and double stranded RNA, enabling effective and efficient experiments for the development of asthma and COPD treating agents.

DISCLOSURE OF INVENTION

Technical Problem

It is an object of the present invention to provide an agent containing FGF 2 as an effective ingredient for the prevention and the treatment of asthma and COPD.

It is another object of the present invention to provide a Th1 asthma or COPD mouse model induced by allergens such as ovalbumin (OA) and double stranded RNA (dsRNA).

Technical Solution

The present invention provides an agent for the prevention and the treatment of asthma containing FGF2 (Fibroblast Growth Factor-2) as an effective ingredient.

The present invention provides an agent for the prevention and the treatment of asthma characteristically induced by the over-expression of IL-13 (Interleukin-13).

The present invention provides an agent for the prevention and the treatment of asthma characteristically induced by the over-expression of IFN-γ (Interferon-γ).

The present invention provides an agent for the prevention and the treatment of asthma containing FGF2 for the purpose of inhibiting IL-13 activity.

The present invention provides an agent for the prevention and the treatment of asthma containing FGF2 for the purpose of inhibiting VEGF activity.

The present invention provides an agent for the prevention and the treatment of asthma containing FGF2 for the purpose of suppressing TGF-β1 (Transforming Growth Factor-β1) activity.

The present invention provides an agent for the prevention and the treatment of COPD containing FGF2 (Fibroblast Growth Factor-2) as an effective ingredient.

The present invention provides an agent for the prevention and the treatment of COPD characteristically induced by the over-expression of IFN-γ(Interferon-γ).

The present invention provides a preparation method for a Th1 asthma or COPD animal model which is characterized by the direct administration of allergens such as ovalbumin and double stranded RNA into airway.

The present invention provides a preparation method for a Th1 asthma or COPD animal model in which the animal is a mouse.

The present invention provides a preparation method for a Th1 asthma or COPD animal model comprising the following steps:

(1) Sensitizing BALB/c mouse by the intranasal administration of 5-15 ☐of polyinosinic-polycytidylic acid, double stranded RNA, and 50-100 ☐of ovalbumin four times; and Sensitizing the mouse by 25-75 μg of ovalbumin 10 days after the first sensitization The present invention provides a preparation method for a Th1 asthma or COPD animal model in which 10 ☐of double stranded RNA is used for sensitizing the animal in the above step (1).

The present invention provides a preparation method for a Th1 asthma or COPD animal model in which 75 ☐of ovalbumin is used for sensitizing the animal in the above step (1) and 50 ☐of ovalbumin is used for sensitizing the animal, 10 days later, in the above step (2).

The present invention provides a preparation method for a Th1 asthma or COPD animal model in which the asthma is non-eosinophilic.

The present invention provides a Th1 asthma or COPD animal model generated by the method of the present invention.

The present invention provides a Th1 asthma or COPD animal model in which the animal is a mouse.

The present invention provides an IL-13, VEGF or TGF-β1 inhibitor containing FGF2 (Fibroblast Growth Factor-2) as an effective ingredient.

The present invention provides an inhibitor for fibrosis, airway inflammation, AHR or airway remodeling, containing FGF2 (Fibroblast Growth Factor-2) as effective ingredient.

Hereinafter, the present invention is described in detail.

The present invention provides a pharmaceutical composition for the prevention or the treatment of asthma containing FGF2 as an effective ingredient. More precisely, the present invention provides an agent for the prevention and the treatment of asthma which is induced characteristically by the over-expression of IL-13 (Interleukin-13) or IFN-γ(Interferon-γ). The agent provided by the present invention characteristically inhibits the activities of IL-13 (Interleukin-13), VEGF or TGF-β1 (Transforming Growth Factor-β1).

Asthma is divided into bronchial asthma, cardiac asthma, etc, but simply bronchial asthma is regarded as asthma. Asthma is characterized by airway hyperresponsiveness and airway remodeling.

Airway remodeling is initiated by the increased immune response against allergen, inflammation or stimuli. Once the immune response is increased, T-cells secret cytokine, an intracellular signal transmitter. The secreted cytokine induces the migration of inflammatory cells into tissues, causing chronic inflammation in airway, resulting the structural alterations in airway.

AHR is also believed to be a critical factor for pathogenesis of asthma, which distinguishes asthma from other respiratory diseases. AHR accompanies airway smooth muscle hyperplasia, contractility and fibrosis of epithelial cells and pulmonary parenchyma, which are the characteristics of airway remodeling. Therefore, airway inflammation, AHR and airway remodeling are closely related each other, namely, treating one of those symptoms might result in the unexpected treatment of other symptoms and the same agent can be applied to all of airway inflammation, AHR and airway remodeling.

The level of AHR shown in Th2 cytokine IL-4 transgenic mice (IL-4 TG(+)) was similar to that in wild type (WT) controls (FIG. 1A), while the level of AHR shown in Th2 cytokine IL-9 transgenic mice (IL-9(+)/IL-13 (+/+)) was increased, compared to that in wild type controls. However, AHR was inhibited in IL-13 knock-out mice (IL-9(+)/IL-13 (−/−)), suggesting that asthma induced by IL-9 over-expression was mediated by IL-13 (see FIG. 1B).

In order to confirm the above finding, IL-13 transgenic mice were prepared to investigate the relationship between airway hyperresponsiveness and TGF-β1 and VEGF, known to be over-expressed by IL-13. As a result, AHR was enhanced in IL-13 transgenic mice, compared to that in wild type controls (see FIG. 2).

The concentrations of TGF-β1 and VEGF were also increased in bronchoalveolar lavage (BAL) of IL-13 transgenic mice, meaning that IL-13 induced AHR is regulated by downstream molecules like TGF-β1 and VEGF.

The regulation of IL-13 mediated AHR by downstream molecule, VEGF, was proved by confirming that IL-13 mediated AHR was inhibited by the action of SU1498, a signaling blocker of receptor 2 (see FIG. 4).

The role of FGF2 in pathogenesis of IL-13 mediated asthma has not been elucidated. Thus, the present inventors made efforts to explain the role of FGF2 and at last confirmed that FGF2 is very effective for the treatment of characteristic symptoms of asthma induced by VEGF and TGF-β1 whose levels are regulated by IL-13. Blocking FGF2 resulted in the increase of VEGF concentration (see FIG. 5) in an animal model and further caused AHR (see FIG. 6). This result is coincident with the finding of other experiments, which is blocking VEGF results in the inhibition of AHR (see FIG. 6) in a mouse deficient in FGF2.

Pharmaceutical effect of FGF2 on IL-13 or VEGF induced asthma is supported by following finding.

FGF2 was intra-nasally administered to an IL-13 mediated Th2 asthma model, followed by investigation on the effect of FGF2. As a result, FGF2 reduced airway hyperreponsiveness to methacholine (see FIG. 20), reduced the number of inflammatory cells in bronchoalveolar lavage (BAL) (see FIG. 21), and inhibited the expressions of IL-13 and VEGF (see FIG. 22), both are key mediators for Th2 asthma. From the results of histological test, it was confirmed that FGF2 reduced hypertrophy and obliteration of bronchial wall almost to the normal conditions of lung tissues (see FIG. 23). In conclusion, FGF2 was confirmed to inhibit the expressions of VEGF and IL-13, resulting in the suppression of AHR and inflammation. Therefore, FGF2 can be effectively used for the treatment of asthma.

With respect to TGF-β1, a downstream molecule affecting IL-13 mediated asthma, previous studies reported that airway remodeling was observed in TGF-β1 transgenic mice (Lee et al., J. Exp. Med., 200: 377-389, 2004) and bronchial fibrosis initiated by IL-13 depended on TGF-β1 (Lee et al., J. Exp. Med. 194: 809-821, 2001). TGF-β1 seriously induced airway resistance and obliteration in TGF-β1 transgenic mice (see FIG. 7) and AHR was suppressed by methacholine (see FIG. 8).

In order to confirm the relation between FGF2 and TGF-β1 in IL-13 mediated asthma, AHR was measured in FGF2 knock-out mice. As a result, the inhibition of AHR by TGF-β1 was not observed in FGF2 knock-out mice (see FIG. 9). The result indicates that the inhibition of AHR is not by TGF-β1 itself but by FGF2 co-expressed with TGF-β1. That is, the increase of TGF-β1 in the presence of FGF2 reduces AHR, but TGF-β1 cannot suppress the elevation of AHR in the absence of FGF2.

From the above results was confirmed the association of FGF2 with TGF-β1 as follows; once airway tissues are injured, immune system begins to work. Airway smooth muscle cells and fibroblasts are transformed into myofibroblasts, resulting in the inducement of fibrosis. At this time, FGF2 induces the proliferation of airway smooth muscle cells and fibroblasts to supplement the deficiency by TGF-β1 and induces at the same time transformation of myofibroblasts into airway smooth muscle cells and fibroblasts. In conclusion, FGF2 induces the transformation of myofibroblasts into fibroblasts, resulting in the decrease of the number of myofibroblasts, meaning that FGF2 inhibit airway remodeling and at the same time inhibits AHR.

In order to explain the inhibition of airway remodeling by FGF2, the concentration of collagen and AHR were measured in FGF2 knock-out mice. As a result, the number of fibroblasts secreting collagen in lungs of FGF2 knock-out mice was lower than that of wild type controls (see FIG. 10). The result indicates that the number of fibroblasts was reduced because the proliferation of the cells was not induced by FGF2, so that the concentration of collagen secreted in those cells was also reduced. The effect of methacholine on AHR was also investigated. As a result, AHR was not much affected by methacholine in wild type mice, but AHR was elevated greatly in FGF2 knock-out mice (see FIG. 9). The above result indicates that the deficiency in FGF2 during the pathway from IL-13 through TGF-β1 blocks the proliferation of fibroblasts and the transformation of myofibroblasts into fibroblasts, resulting in airway remodeling. And further, the number of fibroblasts sensitively responding to methacholine was continuously decreased to make AHR high. Thus, FGF2 can be effectively used for the treatment of IL-13 and TGF-β1 mediated asthma.

In addition to IL-13, IFN-γ a Th1 cytokine, plays an important role in pathogenesis of asthma. Lots of previous studies supported the idea that a Th1 cytokine, especially IFN-γ is closely associated with asthma. However, no Th1 mediated asthma model has been established, yet. This is because most of asthma studies have been focused on Th1/Th2 hypothesis emphasizing the importance of Th2 activation on asthma pathogenesis. So, asthma models have been created by over-expressing eosinophils or immunoglobulin E (IgE), as of today.

In contrast, according to recent reports, AHR might be induced regardless of eosinophilic inflammation (Venkayya R, Am J Respir Cell Mol Biol 2002; 26: 202-8), and the number of non-eosinophilic asthma patients is more than half of the total asthma patients (Douwes et al., Thorax, 57: 643-8, 2002). Thus, it is required to create a Th1 type asthma model for asthma study.

Thus, the present inventors prepared a Th1 asthma or COPD animal model induced by IFN-γ and investigated the role of FGF2 therein. As a result, the present inventors found that FGF2 can be effectively used for the treatment of IFN-γ mediated asthma and COPD.

Therefore, the present invention provides an agent for the prevention and the treatment of COPD, in addition to an agent for the prevention and the treatment of asthma, containing FGF2 (Fibroblast Growth Factor-2) as effective ingredient. The COPD can be induced by the over-expression of IFN-γ (Interferon-γ).

First, the relation between IFN-γ and FGF2 in IFN-γ mediated asthma was investigated. The expression of FGF2 in the lung of an IFN-γ transgenic mouse was measured by RT-PCR. As a result, the expression of FGF2 was remarkably inhibited in the transgenic mice, unlike in wild type controls (see FIG. 13). The result indicates that the expression of FGF2 is down-regulated by IFN-γ signaling pathway.

Secondly, the role of FGF2 in pathogenesis of airway inflammation and AHR initiated by IFN-γ was investigated. FGF2 gene was eliminated from IFN-γ transgenic mice (IFN-γ(+)/FGF2(+/+)), followed by the measurement of AHR. In addition, the number of inflammatory cells and the level of inflammation related cytokine were also measured. As a result, AHR and inflammation were remarkably elevated in IFN-γ transgenic mice deficient in FGF2 gene (IFN-γ(+)/FGF2(+/+)) (see FIGS. 14A and 14B). The elevated level of VEGF is considered to play an important role in the increase of AHR and inflammation induced by the deficiency in FGF2 in IFN-γ transgenic mice (see FIG. 14C). The above results indicate that FGF2 can also be effectively used for the treatment of IFN-γ induced airway inflammation and AHR.

FGF2 activity was investigated in an IFN-γ mediated Th1 asthma model. As a result, FGF2 reduced AHR to methacholine (see FIG. 27), suggesting that FGF2 can be effectively used for the treatment of IFN-γ mediated asthma.

FGF2 was administered to Th1 asthma and COPD mice, followed by detecting the curative effect of FGF2 therein.

The number of inflammatory cells in BAL (see FIG. 26) and AHR to methacholine (see FIG. 36) was reduced in the mice by the treatment of FGF2.

In addition to AHR, apoptosis of parenchymal cells, a characteristic symptom of COPD, was observed in the mice. AHR and apoptosis of parenchymal cells were affected by the presence or the absence of FGF2. After the administration of FGF2, not only AHR (see FIG. 27) but also parenchymal cell destruction (see FIGS. 28 and 29), induced by IFN-γ was reduced in IFN-γ mice. The administration of FGF2 also resulted in the decrease of tissue damage and alveoli destruction or pulmonary emphysema induced by IFN-γ (see FIGS. 30 and 31).

As explained hereinbefore, in asthma and COPD models, FGF2 reduced AHR and inhibited alveoli destruction, suggesting that FGF2 can be effectively used as an agent for the prevention and the treatment of asthma and COPD.

The agent for the prevention and the treatment of asthma and COPD of the present invention containing FGF2 as an effective ingredient can include the effective ingredient by 0.0001-50 weight % of total weight of the composition.

The therapeutic agent of the present invention can include, in addition to FGF2, one or more effective ingredients having the same or similar function to FGF2.

The therapeutic agent of the present invention can also include, in addition to the above-mentioned effective ingredient, one or more pharmaceutically acceptable carriers for the administration. Pharmaceutically acceptable carriers can be selected or be prepared by mixing more than one ingredients selected from a group consisting of saline, sterilized water, Ringer's solution, buffered saline, dextrose solution, maltodextrose solution, glycerol and ethanol. Other general additives such as antioxidative agent, buffer solution, bacteriostatic agent, etc, can be added. In order to prepare injectable solutions, pills, capsules, granules or tablets, diluents, dispersing agents, surfactants, binders and lubricants can be additionally added. The composition of the present invention can further be prepared in suitable forms for each disease or according to ingredients by following a method represented in Remington's Pharmaceutical Science (the newest edition), Mack Publishing Company, Easton Pa.

The therapeutic agent of the present invention can be administered orally or parenterally (for example, intravenous, hypodermic, intraperitoneal, local or intranasal injection). Parenteral administration is preferred and intranasal administration is more preferred. The effective dosage of the composition can be determined according to weight, age, gender, health condition, diet, administration frequency, administration method, excretion and severity of a disease.

The effective dosage of the therapeutic agent of the present invention is 0.005~10 mg/kg per day, and preferably 0.05~1 mg/kg per day. Administration frequency is once a day or preferably a few times a day.

The therapeutic agent of the present invention can be administered singly or treated along with surgical operation, hormone therapy, chemotherapy and biological reaction regulator, to prevent and treat asthma and COPD.

FGF2 of the present invention was intranasally administered to mice to investigate toxicity. As a result, it was evaluated to be a safe substance since its estimated $LD_{50}$ value was much greater than 1,000 mg/kg in mice.

The present invention further provides a preparation method for a Th1 asthma or COPD animal model which is characterized by the direct administration of allergens such as ovalbumin and double stranded RNA into airway.

The preparation method comprises the following steps:

(1) Sensitizing BALB/c mouse by the intranasal administration of 5-15 ☐of polyinosinic-polycytidylic acid, double stranded RNA, and 50-100 ☐of ovalbumin four times; and (2) Sensitizing the mouse by 25-75 μg of ovalbumin 10 days after the first sensitization.

In the above step (1), the amount of double stranded RNA for sensitization is preferred to be 10 ☐. And the amount of ovalbumin is preferred to be 75 ☐. In the above step (2), the amount of ovalbumin used 10 days later for the second sensitization is preferred to be 50 ☐.

Asthma mentioned herein can be non-eosinophilic.

The present invention provides a Th1 asthma or COPD animal model generated by the above preparation method.

The animal can include all mammals available for biological experiments and a mouse is preferred.

In relation to the production of Th1 asthma or COPD animal model, double-stranded RNA (dsRNA) produced during the viral replication strongly induces IFN-α and IFN-γ type I interferons, showing antiviral activity in vivo (Guidotti et al., Annu. Rev. Immunol., 19: 65-91, 2001). The type 1 interferons promote the productions of IL-12 and IFN-γ and are able to induce acquired immune response by stimulating priming of T-cells and the maturation of dendritic cells (Londhe et al., FEBS Lett., 553: 33-8, 2003). Therefore, the present inventors generated an animal model with asthma induced by Th1 pathway after treating it with dsRNA.

The sequence and the length of dsRNA used for the generation of an animal model are not limited as long as they can induce Th1 asthma. It might be purchased and polyinosinic-polycytidylic acid (polyI:C) is preferred.

In the mouse with asthma induced by Th1 pathway, AHR was elevated (see FIG. 15) and the numbers of lymphocytes, neutrophils and macrophages was increased. But, the number of eosinophils was not increased. As a mediator, only IP-10, which is associated with Th1 activity, was remarkably increased (see FIGS. 16 and 17). The above results indicate that non-eosinophilic airway inflammation is induced by OA and dsRNA. The level of IFN-γ in bronchoalveolar lavage (BAL) and the levels of antigen specific IgG1 and IgG2 in blood were also increased (see FIGS. 18 and 19). In conclusion, airway sensitization by OA and dsRNA was induced by IFN-γ and antigen-specific IgG2a, and antigen-specific IgE was not involved. From the above results, a successful generation of a Th1 asthma animal model was confirmed.

The animal model of the present invention also showed the symptoms of COPD. That is, the size and the volume of the lung were increased, alveolis were destructed, and serious fibrosis was induced from the increase of collagen content (see FIG. 28~FIG. 31).

From the above results, it was confirmed that the Th1 asthma mouse of the present invention can be used as a COPD model as well.

The animal model of the present invention was confirmed to be a Th1 or non-eosinophilic asthma model generated by administrating allergens (ovalbumin, OA) and double-stranded RNA (dsRNA) directly into airway, and be effectively used for the development of an agent for the treatment of asthma and COPD.

BRIEF DESCRIPTION OF THE DRAWINGS

FIG. 1A is a set of graphs showing the AHR observed in IL-4 transgenic mice.

FIG. 1B is a graph showing the AHR observed in IL-9(−)/IL-13(+/+), IL-9(−)/IL-13(−/−), IL-9(+)/IL-13(+/+) and IL-9(+)/IL-13(−/−) transgenic mice.

FIG. 2 is a graph showing the comparison of AHR between IL-13 transgenic mice and wild type controls.

FIG. 3 is a graph showing the comparison of the expression levels of VEGF and TGF-β1 in bronchoalveolar lavage (BAL) between IL-13 transgenic mice and wild type controls.

FIG. 4 is a graph showing the AHR observed after the administration of VEGF receptor-2 inhibitor SU 1498 in IL-13 transgenic mice and in wild type controls.

FIG. 5 is a graph showing the comparison of the expression levels of VEGF and TGF-β1 in bronchoalveolar lavage (BAL) between FGF2 knock-out mice and wild type controls.

FIG. 6 is a graph showing AHR observed in FGF2 or FGF2 and VEGF knock-out mice.

FIG. 7 is a graph showing the comparison of AHR between TGF-β1 transgenic mice and wild type controls.

FIG. 8 is a graph showing the changes of AHR observed, according to time, in TGF-β1 transgenic mice and in wild type controls.

FIG. 9 is a graph showing the changes of AHR, observed after the administration of TGF-β1, according to time, in wild type controls or in FGF2 knock-out mice.

FIG. 10 is a graph showing the comparison of collagen content in pulmonary tissue between FGF2 knock-out mice and wild type controls.

FIG. 11 is a graph showing the comparison of AHR between IFN-γ transgenic mice and wild type controls.

FIG. 12 is a graph showing the expression levels of VEGF in bronchoalveolar lavage (BAL), TGF-β1 and IP-10 in IFN-γ transgenic mice and in wild type controls.

FIG. 13 is an agarose gel photograph showing the expression levels of FGF2 in the lung tissues in IFN-γ transgenic mice and in wild type controls.

FIG. 14A is a graph showing the number of total cells (T), the number of macrophages (M), the number of lymphocytes (L), the number of neutrophils (N), and the number of eosinophils (E) of bronchoalveolar lavage (BAL) in IFN-γ(−)/FGF2(+/+), IFN-γ(−)/FGF2(−/−), IFN-γ(+)/FGF2(+/+) or IFN-γ(+)/FGF2(−/−) transgenic mice.

FIG. 14B is a graph showing the methacholine-dependent AHR observed in IFN-γ(−)/FGF2(+/+), IFN-γ(−)/FGF2(−/−), IFN-γ(+)/FGF2(+/+) or IFN-γ(+)/FGF2(−/−) transgenic mice.

FIG. 14C is a graph showing the expression levels of VEGF, TGF-β1 and IP-10 of bronchoalveolar lavage (BAL) in IFN-γ(−)/FGF2(+/+), IFN-γ(−)/FGF2(−/−), IFN-γ(+)/FGF2(+/+) or IFN-γ(+)/FGF2(−/−) transgenic mice.

FIG. 15 is a graph showing the changes of AHR to methacholine after the administration of an allergen (OA) and dsRNA singly or together.

FIG. 16 is a graph showing the number of total cells, the number of macrophages, the number of lymphocytes, the number of neutrophils and the number of eosinophils in bronchoalveolar lavage (BAL) measured after the administration of an allergen (OA) and dsRNA singly or together.

FIG. 17 is a graph showing the expression levels of cytokines (VEGF, IL-5, IL-13 and IP-10) in bronchoalveolar lavage (BAL) observed after the administration of an allergen (OA) and dsRNA singly or together.

FIG. 18 is a graph showing the expression level of IFN-γ in bronchoalveolar lavage (BAL) after the administration of an allergen (OA) and dsRNA singly or together.

FIG. 19 is a graph showing the production of allergen-specific antibody (IgG1 and IgG2a) in serum after the administration of an allergen (OA) and dsRNA singly or together.

FIG. 20 is a graph showing the methacholine dose-dependent AHR observed after the administration of recombinant FGF2 (rFGF2) in Th2 asthma model mice and in wild type controls.

FIG. 21 is a graph showing the number of total cells, the number of macrophages, the number of lymphocytes, the number of neutrophils and the number of eosinophils in bronchoalveolar lavage (BAL) measured after the administration of recombinant FGF2 (rFGF2) in Th2 asthma mice and in wild type controls.

FIG. 22 is a graph showing the concentrations of cytokines (VEGF, IL-13, IL-5 and IP-10) in bronchoalveolar lavage (BAL) observed after the administration of recombinant FGF2 (rFGF2) in Th2 asthma mice and in wild type controls.

FIG. 23 is a pathological photograph of the lung tissues of Th2 asthma mice and wild type controls before and after the administration of recombinant FGF2 (rFGF2).

FIG. 24 is a graph showing the ratio of eosinophilic to non-eosinophilic in induced sputum of a severe asthma patient.

FIG. 25 is a graph showing the expression patterns of IL-4 and IFN-γ in induced sputum of an asthma patient according to the severity of the disease.

FIG. 26 is a graph showing the number of total cells, the number of macrophages, the number of lymphocytes, the number of neutrophils and the number of eosinophils in bronchoalveolar lavage in the presence or absence of over-expression inducer doxycycline, in conditional IFN-γ transgenic mice and in wild type controls.

FIG. 27 is a graph showing the methacholine-dependent AHR in IFN-γ(−)/FGF2(+/+), IFN-γ(−)/FGF2(−/−), IFN-γ(+)/FGF2(+/+) or IFN-γ(+)/FGF2(−/−) transgenic mice.

FIG. 28 is a photograph showing the size of the lung of IFN-γ transgenic mice affected by the presence or the absence of FGF2.

FIG. 29 is a graph showing the volume change of the lung of transgenic mice IFN-γ according to the presence or the absence of FGF2.

FIG. 30 is a graph showing the degree of fibrosis of the lung of IFN-γ transgenic mice according to the presence or the absence of FGF2.

FIG. 31 is a set of histological examination of lung tissues showing the destruction of parenchyma in IFN-γ transgenic mice according to the presence or the absence of FGF2.

MODE FOR THE INVENTION

Practical and presently preferred embodiments of the present invention are illustrative as shown in the following Examples.

However, it will be appreciated that those skilled in the art, on consideration of this disclosure, may make modifications and improvements within the spirit and scope of the present invention.

EXAMPLE 1

Asthma Induced by IL-13 Over-Expression and the Relevance of VEGF and TGF-β1

In order to investigate the development of asthma by IL-13, IL-13 transgenic mice were generated and AHR was measured in each of them. The effect of IL-13 over-expression on the expressions of TGF-β1 and VEGF was also investigated.

1-1 Generation of IL-13 Transgenic Mice

IL-13 transgenic mice were generated by the conventional method (Zhou Zhu et al., J. Clin. Invest., 103: 779-788, 1999; Tang et al., J. Clin. Invest., 98: 2845-2853, 1996; Ray et al., J. Clin. Invest., 100: 2501-2511, 1997). To make selective expression of an IL-13 candidate gene in airway possible, a construct including IL-13 candidate gene linked to a promoter (B. Stripp and J. Whitsett, University of Cincinnati) inducing the expression of 10 kDa Clara cell protein (CC10) was used. In order to produce an inducible transgenic mouse in which the expression of a foreign gene inserted could be regulated from outside, pKS-CC10-rtTA-hGH was prepared by linking CC10 promoter with reverse tetracycline transactivator (rtTA) and human growth hormone (hGH) gene (Ray et al., J. Clin. Invest., 98: 2501-2511, 1997). The plasmid DNA was purified with Elutip-D column (Schleicher and Schuell Inc, USA) and dialysis was performed with a microinjection buffer (0.5 mM Trsi-HCl, 25 mM EDTA, pH7.5). Crossing of CBA and C57BL/6 mice was performed by intrapronuclei microinjection according to the literature cited herein, and the above plasmid DNA was inserted into the resultant F2 ovum, resulting in the production of a transgenic mouse. 0.5 mg/ml doxycycline (dox) in water was administered to transgenic mice and wild type controls randomly, and then bronchoalveolar lavage (BAL) was obtained from each of them to investigate the level of IL-13 in order to evaluate the transformation.

1-2 AHR in IL-13 Transgenic Mice

In order to confirm the development of asthma in IL-13 transgenic mice, one of the most representative symptoms of asthma, AHR, was observed. AHR can be investigated by dose response slope (DRS, Pediatric Allergy and Immunology, 14; 193, 2003) and enhanced pause (Penh, Mckinley et al., Clinical & Experimental Immunology, 136: 224-231, 2004) according to the conventional method commonly known in this field. Penh is calculated as follows; dividing peak expiratory pressure (PEP) by peak inspiratory pressure (PIP) and then multiplying the calculated number by pause. Particularly, AHR was induced in transgenic mice produced in the above example <1-1> by nebulization with methacholine for three minutes after 24 and 48 hours from the second sensitization. Peak expiratory pressure and peak inspiratory pressure were measured by whole body plethysmography every 10 seconds for 3 minutes, and the average was taken for data (FIG. 2). FIG. 2 shows the results of AHR investigation in IL-13 transgenic mice and in wild type controls.

As shown in FIG. 2, AHR was elevated in IL-13 transgenic mice, compared to wild type controls.

1-3 The Effect of IL-13 Over-Expression on the Expressions of VEGF and TGF-β1

Following experiments were performed to investigate the relevance of AHR induced by IL-13 over-expression with downstream modulator of IL-13 signaling pathway, VEGF and TGF-β1. Cannulation with SP45 tube was performed into the airway of the transgenic mouse prepared in the above Example <1-1> to obtain bronchoalveolar lavage (BAL), which was washed with sterilized saline containing 0.1% BSA and 0.05 mm EDTA, followed by centrifugation. In the obtained BAL supernatant, the levels of VEGF and TGF-β1 were measured by using ELISA kit (CalBiotech, USA) (FIG. 3). FIG. 3 presents a graph showing the expression levels of VEGF and TGF-β1 in bronchoalveolar lavage (BAL) obtained from both IL-13 transgenic mice and wild type controls.

As shown in FIG. 3, the concentrations of TGF-β1 and VEGF were increased in BAL obtained from the transgenic mice having AHR induced by IL-13 over-expression. The result indicates that AHR induced by IL-13 is regulated by downstream modulators TGF-β1 and VEGF, which is supported by the results of the following Example <1-4>.

1-4 Suppression of AHR by a VEGF Blocker

In order to confirm the result of the above Example <1-3>, 10 mg/kg of VEGF receptor-2 blocker SU1498 (EMD Bioscience, USA) was administered into the abdominal cavity of the mouse prepared in the Example <1-1>, once a day (FIG. 4). FIG. 4 presents a graph showing AHR observed in IL-13 transgenic mice and in wild type controls after the administration of VEGF receptor-2 blocker SU1498.

As shown in FIG. 4, AHR induced by IL-13 is suppressed by VEGF receptor-2 blocker, indicating that AHR induced by IL-13 is developed by signal transduction via VEGF.

EXAMPLE 2

The role of FGF2 in Pathogenesis of Asthma Induced by IL-13

In order to investigate the role of FGF2 in pathogenesis of asthma developed by IL-13 and the actions of downstream modulators TGF-β1 and VEGF, AHR and airway remodeling were observed in FGF2 knock-out (−/−) mice.

2-1 AHR Induced by the Deficiency of FGF2

Following experiments were performed to investigate the association of FGF2 with AHR. FGF2 knock-out mice were purchased from Jackson Lab (CA, USA). AHR (DRS) to methacholine and the concentrations of VEGF and TGF-β1, which were proved to be increased in the transgenic mice, in BAL were investigated in the analogy to the procedure as described in the Example <1-2> and Example <1-3> (FIGS. 5 and 6). FIG. 5 presents a graph showing the expression levels of VEGF and TGF-β1 in BAL obtained from both FGF2 knock-out mice and wild type controls. FIG. 6 presents a graph showing AHR observed in FGF2 knock-out mice and FGF2 knock-out mice treated with the VEGF blocker as described in the Example <1-4>.

As shown in FIG. 5, the concentration of VEGF was increased in FGF2 knock-out mice, compared to wild type controls, indicating the elevation of AHR, which was in accordance with the result shown in FIG. 6.

As shown in FIG. 6, AHR was elevated in FGF2 knock-out mice, and AHR could be suppressed by the VEGF blocker. The result indicates that AHR induced by the deficiency of FGF2 is regulated by VEGF, precisely the administration of FGF2 inhibits the expression of VEGF, making it a promising candidate for an agent for the prevention and the treatment of asthma mediated by VEGF pathway.

2-2 Airway Remodeling Initiated by the Deficiency of FGF2

In order to investigate the association of FGF2 with airway remodeling, following experiments including measurement of cell proliferation and transformation, which were accompanied by airway remodeling, were performed.

FGF2 knock-out mice were purchased from Jackson Lab (CA, USA). The lung tissues were taken by the conventional method and the concentration of collagen in the tissues, which could be the index for the measurement of cell proliferation and transformation, was assayed using Sircol Collagen assay kit (Biocolor assay, Northern Ireland) according to the manufacturer s instructions (FIG. 10). FIG. 10 presents a graph showing the concentration of collagen in the lung tissues taken from both FGF2 knock-out mice and wild type controls.

As shown in FIG. 10, the concentration of collagen was much lower in FGF2 knock-out mice than in wild type controls.

In conclusion, the number of fibroblasts secreting collagen in the lung was decreased in FGF2 knock-out mice, which was because fibroblasts were transformed into myofibroblasts and then migrated, resulting in the decrease of the number of fibroblasts. As a result, airway remodeling was induced.

Form the above results, it was confirmed that FGF2 inhibits airway remodeling and AHR, so it can be effectively used for the treatment of asthma.

EXAMPLE 3

Development of Asthma by TGF-β1

In order to investigate pathogenesis of asthma mediated by the expression of TGF-β1 induced by IL-13, TGF-β1 transgenic mice were generated in analogy to the procedure as described in the Example <1-1> and following experiments were performed.

3-1 Airway Remodeling Initiated by TGF-β1

AHR resulted from airway remodeling was investigated in the analogy to the procedure as described in the above Example <1-2> (FIG. 7). FIG. 7 presents a graph showing the comparison of AHR between TGF-β1 transgenic mice and wild type controls according to time. FIG. 8 presents a graph showing the comparison of AHR to methacholine between TGF-β1 transgenic mice and wild type controls according to time.

As shown in FIG. 7, serious airway resistance was induced by TGF-β1, supported from the results of Penh. As shown in FIG. 8, however, AHR to methacholine was inhibited. This result indicates that over-expression of TGF-β1 is involved only in airway remodeling, among characteristic symptoms of asthma.

3-2 The Role of FGF2 in the Inhibition of AHR by TGF-β1

As explained in the above Example 3-1>, AHR in FGF2 knock-out mice was measured to investigate the role of FGF2 in the inhibition of AHR by TGF-β1 (FIG. 9). FIG. 9 presents a graph showing AHR observed in FGF2 knock-out mice and in wild type controls, according to time, after the administration of TGF-β1 (R&D system, USA).

As shown in FIG. 9, the inhibition of AHR by TGF-β1 was weaker in FGF2 knock-out mice, indicating that the inhibition of AHR by TGF-β1 is not because of TGF-β1 itself, but because of FGF2 which is co-expressed with TGF-β1. That is, the inhibition of AHR by the up-regulation of TGF-β1 is associated with FGF2.

EXAMPLE 4

Development of Asthma Initiated by IFN-γ and the Role of FGF2 Therein

An asthma model induced by IFN-γ a key mediator for COPD and severe asthma, was generated. In order to confirm the role of FGF2, following experiments were performed with IFN-γ transgenic mice in the analogy to the procedure as described in the Example 1.

4-1 Elevation of AHR by the Over-Expression of IFN-γ

AHR was measured in the transgenic mice by following the procedure used in the above Example <1-2> (FIG. 11). Then, the levels of AHR, VEGF, TGF-β1 and IP-10 protein whose expression is induced by IFN-γ in BAL, were measured by the same method as used in the above Example <1-3> (FIG. 12). FIG. 11 presents a graph showing the comparison of AHR between IFN-γ transgenic mice and wild type controls.

As shown in FIG. 11, AHR was homogeneously elevated in IFN-γ transgenic mice.

As shown in FIG. 12, the concentrations of VEGF and TGF-β1, induced by IL-13 expressed in Th2, were not increased in the transgenic mice, but IP-10 protein (interferon-inducible protein 10), which is not associated with Th2, was increased. And the results indicate that AHR induced in the transgenic mice in this Example is IFN-γ specific.

4-2 The role of FGF2 in the Development of AHR Induced by the Over-Expression of IFN-γ

The effect of IFN-γ over-expression on FGF2 expression

In order to investigate the role of FGF2 in the development of AHR induced by IFN-γ over-expression, the expression level of FGF2 was measured in IFN-γ transgenic mice (FIG. 13). RNA was extracted from the lung tissues of wild type and transgenic mice by the conventional method, followed by RT (reverse transcription)-PCR. Briefly, the total RNA was extracted from 1 g of lung tissue taken from each wild type and transgenic mice by using TRIzol Reagent (Life Technology, USA) according to the manufacturer's instruction. RT-PCR was performed using the separated total RNA as a template to synthesize cDNA by using RT-PCR kit (Promega, USA). PCR was performed with an upper primer (SEQ ID NO: 1, 5'-ACT CAC ATT CGA AAC CCC AAA C-3') and a lower primer (SEQ ID NO: 2, 5'-CGT CAG ATC GCC TGG AGA C-3') by using 1 μg of the synthesized cDNA as a template to amplify FGF2 specific cDNA. PCR was performed as follows; predenaturation at 95° C. for 8 minutes, denaturation at 95° C. for 1 minute, annealing at 56° C. for 1 minute, polymerization at 72° C. for 1 minute, 35 cycles from denaturation to polymerization, and final extension at 72° C. for 10 minutes. FIG. 13 presents a photograph of agarose gel showing the amplification of FGF2 specific cDNA of the lung tissues of IFN-γ transgenic mice and wild type controls.

As shown in FIG. 13, the expression of FGF2 was inhibited in IFN-γ transgenic mice, indicating that the expression of FGF2 is inhibited by IFN-γ.

The Role of FGF2 on AHR Induced by IFN-γ Over-Expression

In order to examine the role of FGF2 in the pathogenesis of airway inflammation and AHR induced by IFN-γ AHR, the number of inflammatory cells and the level of inflammation involved protein in BAL were measured in mice having different genotypes (FIG. 14). The mice were generated as previously described (Zhou Zhu et al., J. Clin. Invest., 103: 779-788, 1999; Tang et al., J. Clin. Invest., 98: 2845-2853, 1996; Ray et al., J. Clin. Invest., 100: 2501-2511, 1997). In FIG. 14, + means a mouse showing the over-expression of a target gene, − means a mouse deficient in a target gene. FIG. 14A presents a graph showing the number of total cells (Total), the number of macrophages (M), the number of lymphocytes (L), the number of neutrophils (N) and the number of eosinophils (E) in bronchoalveolar lavage taken from IFN-γ(−)/FGF2(+/+), IFN-γ(−)/FGF2(−/−), IFN-γ(+)/FGF2(+/+) and IFN-γ(+)/FGF2(−/−) transgenic mice. FIG. 14B presents a graph showing the methacholine-dependent AHR in IFN-γ(−)/FGF2(+/+), IFN-γ(−)/FGF2(−/−), IFN-γ(+)/FGF2(+/+) or IFN-γ(+)/FGF2(−/−) transgenic mice. FIG. 14C is a graph showing the expression levels of VEGF, TGF-β1 and IP-10 of bronchoalveolar lavage (BAL) in IFN-γ(−)/FGF2(+/+), IFN-γ(−)/FGF2(−/−), IFN-γ(+)/FGF2(+/+) or IFN-γ(+)/FGF2(−/−) transgenic mice.

As shown in FIG. 14, the deficiency in FGF2 gene in IFN-γ transgenic mice results in the elevation of AHR induced by IFN-γ and the increase of inflammatory cell density, making airway inflammation worse. This result indicates that FGF2 can be effectively used for the treatment of asthma initiated by IFN-γ.

EXAMPLE 5

Inhibition of IL-13 Mediated Th2 Asthma by the Administration of FGF2

Following experiments were performed to investigate the inhibitory effect of FGF2 protein on IL-13 mediated Th2 asthma.

Recombinant FGF protein (rFGF2) was purchased from Phamacia-Upjohn Co (Italy).

In order to generate an AHR mouse model, BALB/c mice (Jackson Lab, USA) were sensitized by i.p. injecting 75 ☐of ovalbumin (OA) and 2 mg of alum twice, and 10 days later, the mice were sensitized again by administrating 50 ☐of ovalbumin intranasally to induce asthma. The resultant mice were named as Th2 asthma mice.

The transgenic mice and wild type controls were intranasally administered with 10 ☐/head of rFGF2 once a day for 4 days or not administered (this group was administered only with saline), followed by measuring the levels of AHR to methacholine (FIG. 20), the number of inflammatory cells (FIG. 21), and the concentrations of mediators such as VEGF, IL-13, IL-5 and IP-10 (FIG. 22) according to the procedure as previously described in the above Example <1-2> and Example <1-3>.

FIG. 20 presents a graph showing methacholine dose-dependent AHR observed in Th2 asthma mice and wild type controls after the administration of recombinant FGF2. FIG. 21 is a graph showing the number of total cells, the number of macrophages, the number of lymphocytes, the number of neutrophils and the number of eosinophils in bronchoalveolar lavage (BAL) measured after the administration of recombinant FGF2 (rFGF2) in Th2 asthma mice and in wild type controls. FIG. 22 is a graph showing the concentrations of cytokines (VEGF, IL-13, IL-5 and IP-10) in bronchoalveolar lavage (BAL) observed after the administration of recombinant FGF2 (rFGF2) in Th2 asthma mice and in wild type controls.

As shown in FIG. 20, inhibition effect on AHR to methacholine was much clear in rFGF2 treating Th2 asthma mice, comparing in rFGF2 non-treating Th2 asthma mice.

As shown in FIG. 21, the number of inflammatory cells in BAL was much more reduced in rFGF2 treating Th2 asthma mice than in rFGF non-treating Th2 asthma mice.

As shown in FIG. 22, the concentrations of IL-13 and VEGF, key mediators for Th2 asthma, were much lowered in rFGF2 treating Th2 asthma mice than in rFGF non-treating Th2 asthma mice. However, the expressions of IL-5 and IP-10, which were known to be not associated with Th2 asthma, were not changed.

Histological assay was also performed with bronchial wall of asthma mice after the treatment of rFGF2 (FIG. 23). FIG. 23 presents a pathological photograph of the lung tissues of Th2 asthma mice and wild type controls before (A) and after (B) the administration of recombinant FGF2 (rFGF2).

As shown in FIG. 23, as a result of histological assay (B) with bronchial wall of rFGF2 treating mice, hypertrophy and obliteration of bronchial wall were reduced by the administration of rFGF2 to the normal level (C).

From the above results, it was confirmed that FGF2 inhibits the expressions of VEGF and IL-13, resulting in the inhibition of Th2 mediated AHR and airway inflammation. Thus, FGF2 can be effectively used for the prevention and the treatment of asthma.

EXAMPLE 6

Inhibition of IFN-γ Mediated Th1 Asthma and COPD by the Administration of FGF2

Following experiments were performed to investigate the inhibition activity of FGF2 in IFN-γ mediated Th1 asthma mice.

Recombinant FGF2 protein was purchased from Pharmacia-Upjohn Co. (Italy). IFN-γ mediated Th1 asthma mice were generated as follows.

6-1 Generation of Th1 Asthma and COPD Animal Models by Using Ovalbumin and Double Stranded RNA BALB/c mice (Jackson Lab, USA) were sensitized by administrating 10 ☐ of synthesized dsRNA ployinosinic-polycytidylic acid (PolyIC, Sigma, USA) and 75 ☐ of ovalbumin (OA) intranasally, singly or together, four times. 10 days later, the mice were challenged with the intranasal administration of 50 ☐ of OA to induce asthma. The resultant mice were named Th1 asthma mice. The negative control mice were administered only with phosphate buffered saline (PBS).

1) Confirmation of Characteristics of Th1 Asthma

In order to confirm whether or not Th1 asthma was induced in the mice, AHR to methacholine (FIG. 15), the number of inflammatory cells in BAL (FIG. 16) and the concentrations of mediators such as VEGF, IL-13, IL-5 and IP-10 (FIG. 17) were measured according to the procedure as described in the Example <1-2> and Example <1-3>.

FIG. 15 is a graph showing the changes of AHR to methacholine after the administration of allergen (OA) and dsRNA singly or together. FIG. 16 is a graph showing the number of total cells, the number of macrophages, the number of lymphocytes, the number of neutrophils and the number of eosinophils in bronchoalveolar lavage (BAL) measured after the administration of allergen (OA) and dsRNA singly or together. FIG. 17 is a graph showing the expression levels of cytokines (VEGF, IL-5, IL-13 and IP-10) in bronchoalveolar lavage (BAL) observed after the administration of allergen (OA) and dsRNA singly or together.

As shown in FIG. 15, AHR to methacholine was elevated in asthma mice induced by OA and dsRNA.

As shown in FIG. 16, the numbers of lymphocytes, neutrophils and macrophages were increased in the mice but the number of eosinophils was not changed.

As shown in FIG. 17, as a mediator, IP-10 was only increased remarkably in the mice.

The above results indicate that non-eosinophilic airway inflammation was induced by OA and dsRNA.

In addition, in order to confirm whether the above Th1 asthma was induced by IFN-γ the levels of IFN-γ IgG1 and IgG2a in bronchoalveolar lavage (BAL) were measured (FIG. 18 and FIG. 19). FIG. 18 presents a graph showing the expression level of IFN-γ in BAL when OA and dsRNA were administered singly or together. FIG. 19 presents a graph showing the production of allergen specific antibodies (IgG1 and IgG2a) in serum when OA and dsRNA were administered singly or together.

As shown in FIG. 18 and FIG. 19, the level of IFN-γ in BAL was at least three-fold increased, and the levels of IgG1 and IgG2 in serum were also increased. The above results indicate that asthma induced by OV and dsRNA was associated with IFN-γ and antigen-specific IgG2a and was not related to IgE which is involved in Th2 asthma.

(2) Confirmation of Characteristics of COPD

In order to confirm whether COPD was induced in the above mice, the size and the volume of the lung and the concentration of collagen were measured (FIG. 28, FIG. 29 and FIG. 30). FIG. 28D presents a graph showing the size of the lung of the mice. FIG. 29D presents a graph showing the volume of the lung of the mice. FIG. 30D presents a graph showing the level of fibrosis in the lung of the transgenic mice.

As shown in FIG. 28D, FIG. 29D and FIG. 30D, the size and the volume of the lung and the concentration of collagen were remarkably increased in Th1 asthma mice, suggesting that the mice have characteristics of COPD. With the increase of the size and volume of the lung and the concentration of collagen, lung tissue damage, alveoli destruction and pulmonary emphysema are the typical symptoms of COPD, which was also accompanied by the mice, as shown in FIG. 31.

FIG. 31A presents a pathological photograph of lung tissues showing the destruction of parenchyma in Th1 asthma mice. As shown in FIG. 31, the enlargement of alveoli area caused by the destruction of parenchyma, which is one of the typical symptoms of COPD, was observed in the lung of IFN-γ transgenic mice.

The increase of the size and the volume of the lung and apoptosis in alveoli along with the increase of collagen content confirmed the serious fibrosis.

From the above results, it was confirmed that Th1 asthma mice can be effectively used as a COPD model showing COPD pathogenesis.

6-2 Inhibition of Th1 Asthma by the Administration of FGF2

Following experiments were performed to investigate whether or not FGF2 protein could inhibit asthma in IFN-γ mediated Th1 asthma mice. The mice generated in the above Example <6-1> were named Th1 asthma experimental mice group. Recombinant FGF2 was administered to Th1 asthma mice generated in the Example <6-1> and wild type controls according to the same procedure as used in the Example 5. Then, AHR to methacholine was measured in both groups by following the procedure described in the Example <1-2>.

FIG. 27 presents a graph showing methacholine dose-dependent AHR observed in Th1 asthma mice and in wild type controls, after the administration of rFGF2.

As shown in FIG. 27, AHR to methacholine was much lower in rFGF2 treated mice than in rFGF2 not treated mice.

FIG. 28 presents a photograph showing the comparison of the size of the lung between rFGF2 treating Th1 asthma mice and rFGF2 not treating mice As shown in FIG. 28, the size of the lung of rFGF2 treating mice was smaller than that of rFGF2 not treating Th1 asthma mice.

The above results indicate that FGF2 reduces characteristic asthma symptoms in IFN-γ transgenic mice, so that it can be effectively used for the treatment of IFN-γ induced asthma.

6-3 Inhibition of COPD by the Administration of FGF2

Following experiments were performed to investigate inhibition effect of FGF2 on COPD. Recombinant FGF2 was administered to both transgenic mice generated in the above Example <6-1> and wild type controls according to the procedure as described in the Example 5. Then, the size and the volume of the lung and the concentration of collagen, which are major index for COPD, were measured in those mice (FIG. 28, FIG. 29 and FIG. 30). FIGS. 28A, B, C and D show the size of the lung of each normal and COPD mouse, and the volumes of the lung of them were shown in the graph of FIG. 29. FIGS. 30A, B, C and D are graphs showing the levels of fibrosis in the lungs of wild type controls and of COPD mice after the administration of rFGF or non-administration. FIG. 31 presents a set of pathological photographs of lung tissues showing the destruction of parenchyma in IFN-γ transgenic mice according to the presence or the absence of FGF2.

As shown in FIGS. 28C and D, and in FIGS. 29C and D, the volume of the lung was remarkably decreased after the administration of rFGF2. As shown in FIGS. 30C and D, the concentration of collagen was also decreased significantly with the administration of rFGF2 in COPD mice. The decrease of the size and the volume of the lung and the decrease of collagen content suggested that rFGF2 could be effectively used for the treatment of COPD, as shown in FIG. 31.

FIG. 31 presents a set of pathological photographs of lung tissues showing the destruction of parenchyma in COPD mice. As shown in FIG. 31A, the enlargement of alveoli area caused by apoptosis of parenchyma, a typical symptom of COPD patients, was observed in the lung of rFGF2 non-treating mice (B), unlike the lung of rFGF2 treating group (A), indicating that the administration of rFGF2 is effective for the treatment of COPD.

Form the above results, it was confirmed that the size and the volume of the lung, apoptosis in alveoli and the collagen content are all involved in fibrosis in COPD mice, and FGF2 administration is effective for the treatment of those pathological symptoms.

EXAMPLE 7

Over-Expression of IFN-γ in a Human Asthma Model

Following experiments were performed to investigate whether or not human asthma could be induced by the over-expression of IFN-γ and non-eosinophilic cells. Sputum was taken from 215 adult asthma patients showing reversible airway obstruction, and their vital capacities were measured using sprimetry according to the conventional method. Methacholine bronchial challenge was also performed to test pulmonary function (FIG. 24). FIG. 24 presents a graph showing the ratio of eosinophilic to non-eosinophilic in induced sputum of a severe asthma patient. As shown in FIG. 24, more than half of the patients were confirmed to have non-eosinophilic asthma, rather than eosinophilic asthma.

In order to confirm asthma mediating factors, the levels of IL-4 and IFN-γ were measured (FIG. 25). FIG. 25 is a graph showing the expression patterns of IL-4 and IFN-γ in induced sputum of an asthma patient according to the severity of the disease.

As shown in FIG. 25, the expression of IFN-γ which is related to Th1 asthma, was increased in severe asthma patients, but the expression of IL-4, which is related to Th2 asthma, was not changed. This result indicates that human asthma patients, in particular with severe asthma, have IFN-γ mediated non-eosinophilic Th1 asthma.

INDUSTRIAL APPLICABILITY

As explained hereinbefore, the therapeutic agent of the present invention containing FGF2 as an effective ingredient can be effectively used for the prevention and the treatment of fibrosis, airway inflammation, airway hyperresponsivess, airway remodeling, asthma and COPD. In addition, the asthma and COPD animal models developed by using ovalbumin and double stranded RNA can also be effectively used for the development of a therapeutic agent for asthma and COPD.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

The invention claimed is:

1. A method for treating chronic obstructive pulmonary disease (COPD) in a subject comprising administering a pharmaceutically effective amount of FGF2 (Fibroblast Growth Factor-2) to the subject, wherein the COPD is induced by IFN-γ (Interferon-γ) over-expression.

* * * * *